(12) United States Patent
Khleif et al.

(10) Patent No.: US 10,292,978 B2
(45) Date of Patent: *May 21, 2019

(54) SPECIFIC AKT3 INHIBITOR AND USES THEREOF

(71) Applicant: Augusta University Research Institute, Inc., Augusta, GA (US)

(72) Inventors: Samir N. Khleif, Silver Spring, MD (US); Mikayel Mkrtichyan, Millbrae, CA (US); Iryna Lebedyeva, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,659

(22) Filed: Jan. 17, 2017

(65) Prior Publication Data
US 2017/0202829 A1    Jul. 20, 2017

Related U.S. Application Data

(60) Provisional application No. 62/279,248, filed on Jan. 15, 2016.

(51) Int. Cl.
*A61K 31/4709* (2006.01)
*A61K 45/06* (2006.01)

(52) U.S. Cl.
CPC .......... *A61K 31/4709* (2013.01); *A61K 45/06* (2013.01)

(58) Field of Classification Search
CPC ................................................ A61K 31/4709
USPC ........................................................ 514/313
See application file for complete search history.

(56) References Cited

PUBLICATIONS

Taha, Journal of Computer-Aided Molecular Design (2014), 28(5), 509-547.*
Kaminski, Cell reports (2012), 2(5), 1300-15 and.*
Maciolek, Current Opinion in Immunology (2014), 27, 60-74.*
Bell, Biochemistry (2013), 52(51), 9269-9274. AND Suppl.*
Bach, Jean-Francois, "The Effect of Infections on Susceptibility to Autoimmune and Allergic Diseases", N Eng J Med, 347:911-920 (2002).
Bluestone, Jeffrey, A., et al., "Natural Versus Adaptive Regulatory T Cells", Nat Rev Immunol, 3, 253-257 (2003).
Boland, E., et al., "Mapping of Deletion and Translocation Breakpoints in 1q44 Implicates the Serine/Theonine Kinase AKT3 in Postnatal Microcephaly and Agenesis of the Corpus Callosum", American Journal of Human Genetics, 81, 292-303 (2007).
Carson, Bryan D., et al., "Impaired T Cell Receptor Signaling in Foxp3+ CD4 T Cells", Annals of the New York Academy of Sciences, 1103, 167-178 (2007).
Crellin, Natasha, K., et al., "Altered Activation of AKT is Required for the Suppressive Function of Human CD4+CD25+ T Regulatory Cells", Blood, 109, 2014-2022 (2007a).
Crellin, Natasha, K., et al., "Flow Cytometry-Based Methods for Studying Signaling in Human CD4+CD25+ FOXP3+ T Regulatory Cells", Journal of Immunological Methods, 324, 92-104 (2007b).
Dannull, J., et al., "Enhancement of Vaccine-Mediated Antitumor Immunity in Cancer Patients After Depletion of Regulatory T Cells", The Journal of Clinical Investigation, 115, 3623-3633 (2005).
Debosch, B., et al., "Akt2 Regulates Cardiac Metabolism and Cardiomyocyte Survival", J Biol Chem, 281, 32841-32851 (2006).
Emamian, E.S., et al., "Convergent Evidence for Impaired AKT1-GSK3β Signaling in Schizophrenia", Nat Genet, 36, 131-137 (2004).
Fontenot, Jason, D., et al., "Foxp3 Programs the Development and Function of CD4+CD25+ Regulatory T Cells", Nat Immunol, 4(4):330-6 (2003).
Franke, Thomas F., "Intracellular Signaling by Akt: Bound to Be Specific", Science 1, pe29 (2008).
Garofalo, R.S. et al., "Severe Diabetes, Age-Dependent Loss of Adipose Tissue, and Mild Growth Deficiency in Mice Lacking Akt2/PKBβ", The Journal of Clinical Investigation, 112, 197-208 (2003).
George, S. et al., "A Family with Severe Insulin Resistance and Diabetes Mellitus due to a Missense Mutation in AKT2", Science, 304, 1325-1328 (2004).
Glisic, S., et al., "Inducible Regulatory T Cells (iTregs) from Recent-Onset Type 1 Diabetes Subjects Show Increased in vitro Suppression and Higher ITCH Levels Compared with Controls", Cell and Tissue Research, 339, 585-595 (2010).
Haribhai, D., et al., "A Requisite Role for Induced Regulatory T Cells in Tolerance Based on Expanding Antigen Receptor Diversity", Immunity, 35(1):109-122 (2011).
Haxhinasto, S., et al., "The AKT-mTOR Axis Regulates de novo Differentiation of CD4+Foxp3+ Cells", J Exp Med, 205, 565-574 (2008).
Hori, S., et al., "Control of Regulatory T Cell Development by the Transcription Factor Foxp3", Science, 299, 1057-1061 (2003).
Khattri, R., et al., "An Essential Role for Scurfin in CD4+CD25+ T Regulatory Cells", Nat Immunol, 4(4):337-42 (2003).
Kim, Jiyeon S., et al., "Natural and Inducible TH17 Cells are Regulated Differently by Akt and mTOR Pathways", Nat Immunol, 14(6):611-8 (2013).
Li, L. et al., "CD4+CD25+ Regulatory T-Cell Lines from Human Cord Blood Have Functional and Molecular Properties of T-Cell Anergy", Blood, 106, 3068-3073 (2005).
Liang J., et al., "Design of New Oxazaphosphorine Anticancer Drugs", Curr Pharm Des, 13(9):963-78 Review (2007),
Nakatani, K., et al., "Up-Regulation of Akt3 in Estrogen Receptor-Deficient Breast Cancers and Androgen-Independent Prostate Cancer Lines", The Journal of Biological Chemistry, 274, 21528-21532 (1999).

(Continued)

*Primary Examiner* — Nizal S Chandrakumar
(74) *Attorney, Agent, or Firm* — Smith, Gambrell & Russell, LLP; Charles Vorndran

(57) ABSTRACT

Methods of selectively inhibiting Akt3 are provided. It has been discovered that 4-[(6-nitroquinolin-4-yl)amino]-N-[4-(pyridin-4-ylamino)phenyl]benzamide selectively inhibits Akt3. Because Akt3 modulates the suppressive function of natural Tregs and the polarization of induced Tregs, 4-[(6-nitroquinolin-4-yl)amino]-N-[4-(pyridin-4-ylamino)phenyl]benzamide can be used for modulating immune responses.

9 Claims, 15 Drawing Sheets

Specification includes a Sequence Listing.

(56) References Cited

PUBLICATIONS

Parry, Richard, V., et al., "Signalling to Suit Function: Tailoring Phosphoinositide 3-Kinese During T-Cell Activation", Trends in Immunology, 28, 161-168 (2007).
Patton, D.T., et al., "Cutting Edge: The Phosphoinositide 3-Kinase p110δ is Critical for the Function ofCD4+CD25+Foxp3+ Regulatory T Cells", J Immunology, 177, 6598-6602 (2006).
Patton, D.T., et al., "The P13K p110δ Controls T-Cell Development, Differentiation and Regulation", Biochem Soc Trans, 35, 167-171 (2007).
Roberts S., et al. "Conventional and Unconventional T Cells", Clinical and Basic Immunodermatology, pp. 85-104, (Gaspari and Tyring (ed.)), Springer London (2008).
Romano, G., "The Role of the Dysfunctional Akt-Related Pathway in Cancer: Establishment and Maintenance of a Malignant Cell Phenotype, Resistance to Therapy, and Future Strategies for Drug Development", Scientifica, vol. 2013: Article ID 317186 (2013).
Sakaguchi, S., et al., "Immunologic Self-Tolerance Maintained by Activated T Cells Expressing IL2 Receptor Alpha-Chains (CD25). Breakdown of a Single Mechanism of Self-Tolerance Causes Various Autoimmune Diseases", J Immunol, 155, 1151-1164 (1995).
Sakaguchi, S., "Regulatory T Cells: Key Controllers of Immunologic Self-Tolerance", Cell, 101, 455-458 (2000).
Sakagushi, S., et al., "Foxp3+CD25+CD4+ Natural Regulatory T Cells in Dominant Self-Tolerance and Autoimmune Disease", Immunol, Rev, 212, 8-27 (2006).
Sakagushi, S., et al., "Naturally Arising Foxp3-Expressing CD25+ CD24+ Regulatory T Cells in Self-Tolerance and Autoimmune Disease", Curr Top Microbiol Immunol, 305, 51-66 (2006).
Sakaguchi, S., et al., "Regulatory T Cells and Immune Tolerance", Cell, 133, 775-787 (2008).
Sauer, S., et al., "T Cell Receptor Signaling Controls Foxp3 Expression via P13K, Akt, and mTOR", Proc Natl Acad Sci USA, 105, 7797-7802 (2008).
Schmidt, A., et al., "Molecular Mechanisms of Treg-Mediated T Cell Suppression", Front Immunol, 3:51 (2012).
Tschopp, O., et al., "Essential Role of Protein Kinase by(PKBy/Akt3) in Postnatal Brain Development but not in Glucose Homeostasis", Development (Cambridge, England), 132, 2943-2954 (2005).
Tsiperson, V. et al., "Suppression of Inflammatory Responses during MOG-Induced Experimental Autoimmune Encephalomyelitis is Regulated by AKT3 Signaling", J Immunol, 190(4):1528-39 (2013).
Walsh, Patrick, T., et al., "PTEN Inhibits IL-2 Receptor-Mediated Expansion of CD4+CD25+ Tregs", J Clin Invest, 116, 2521-2531 (2006).
Yang, Zhong-Zhou, et al., "Protein Kinase Bα/Akt1 Regulates Placental Development and Fetal Growth", J Biol Chem, 278, 32124-32131 (2003).
U.S. Appl. No. 15/407,600, filed Jan. 17, (2017).

* cited by examiner

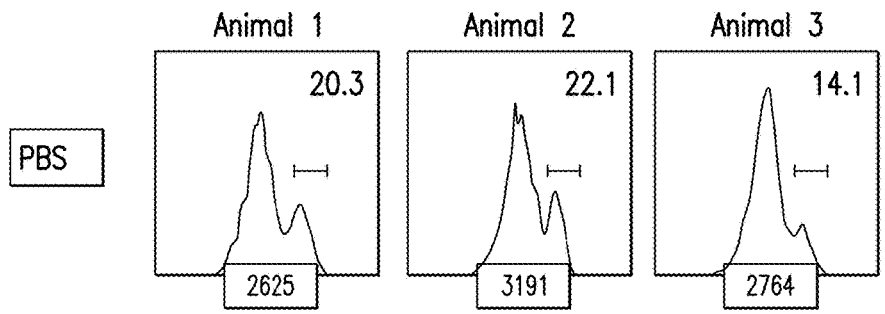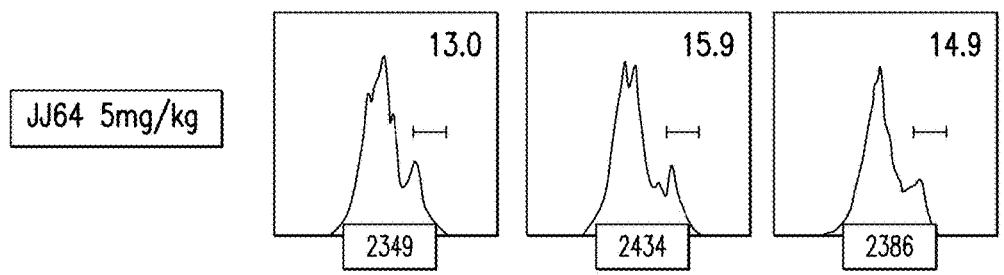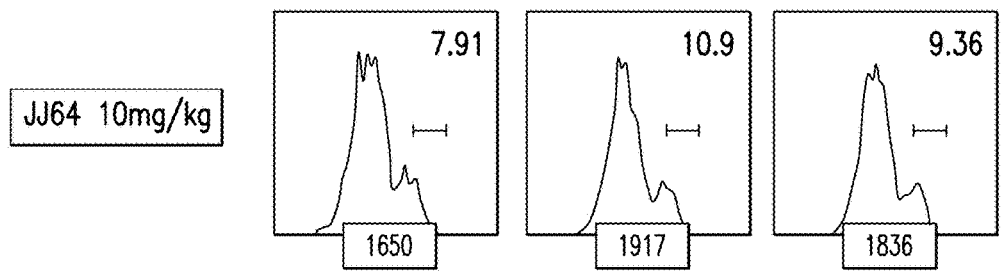

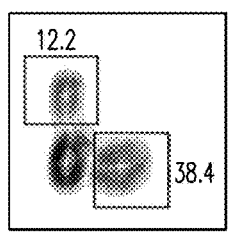
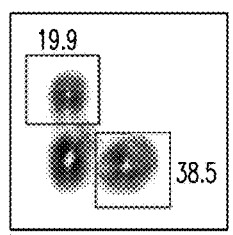
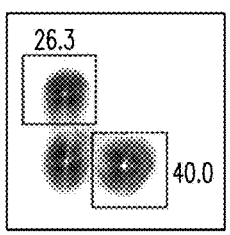
FIG. 4B   FIG. 4C   FIG. 4D
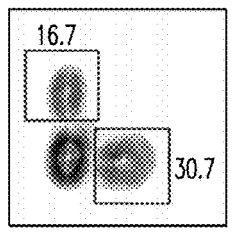
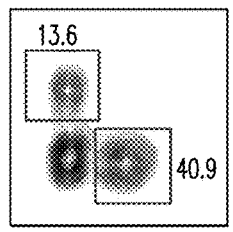
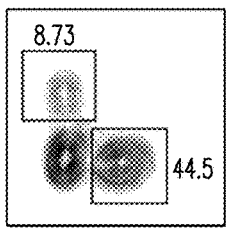
FIG. 4E   FIG. 4F   FIG. 4G
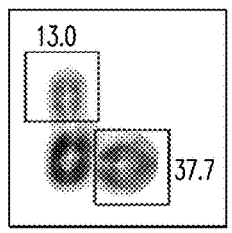
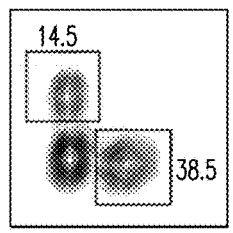
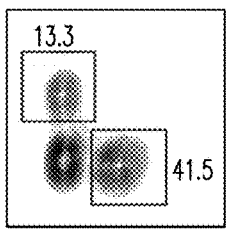
FIG. 4H   FIG. 4I   FIG. 4J

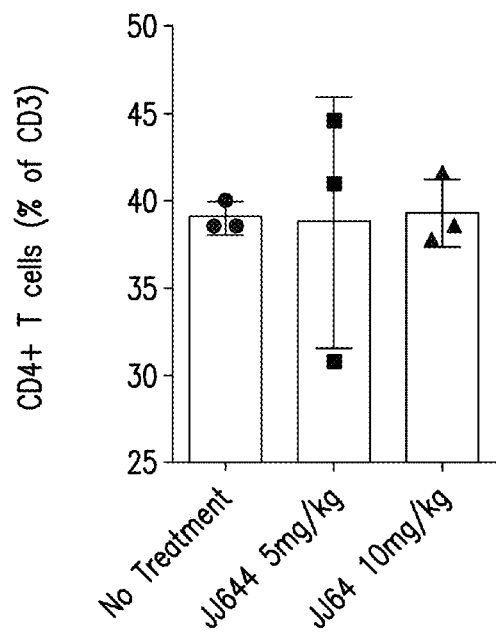 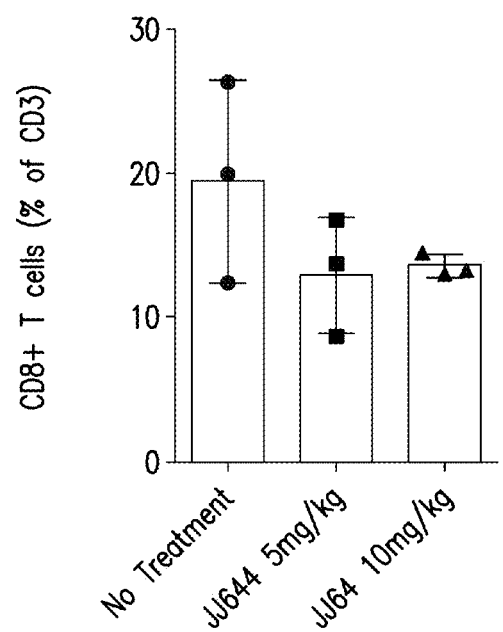
FIG. 4K    FIG. 4L
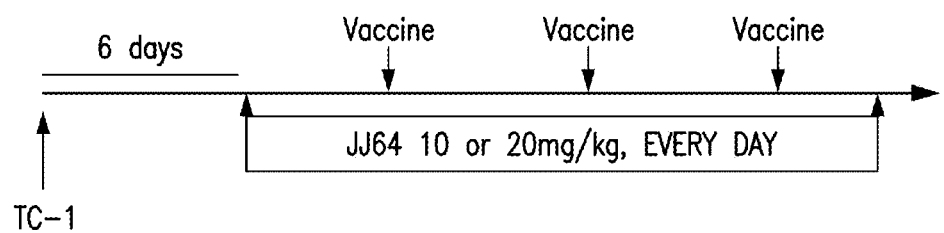
FIG. 5A

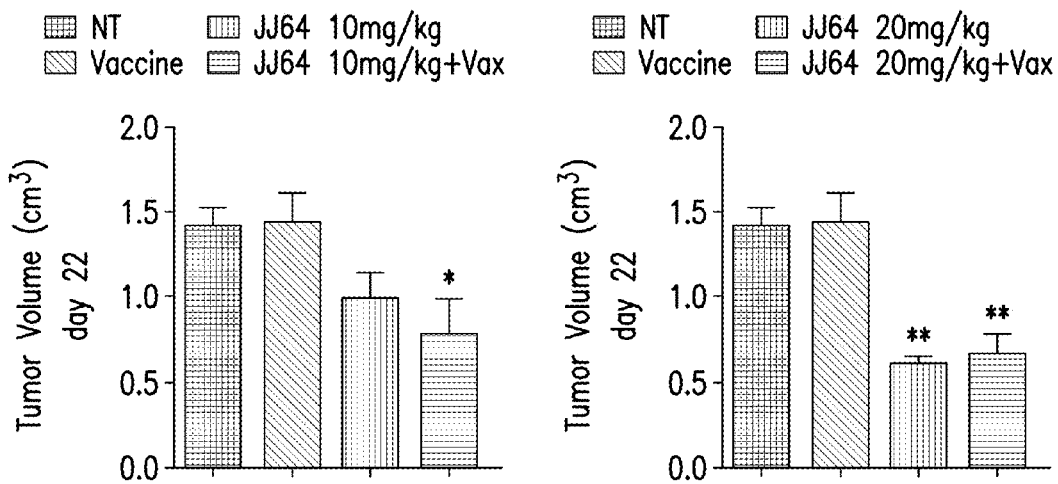
FIG. 5B
FIG. 5C
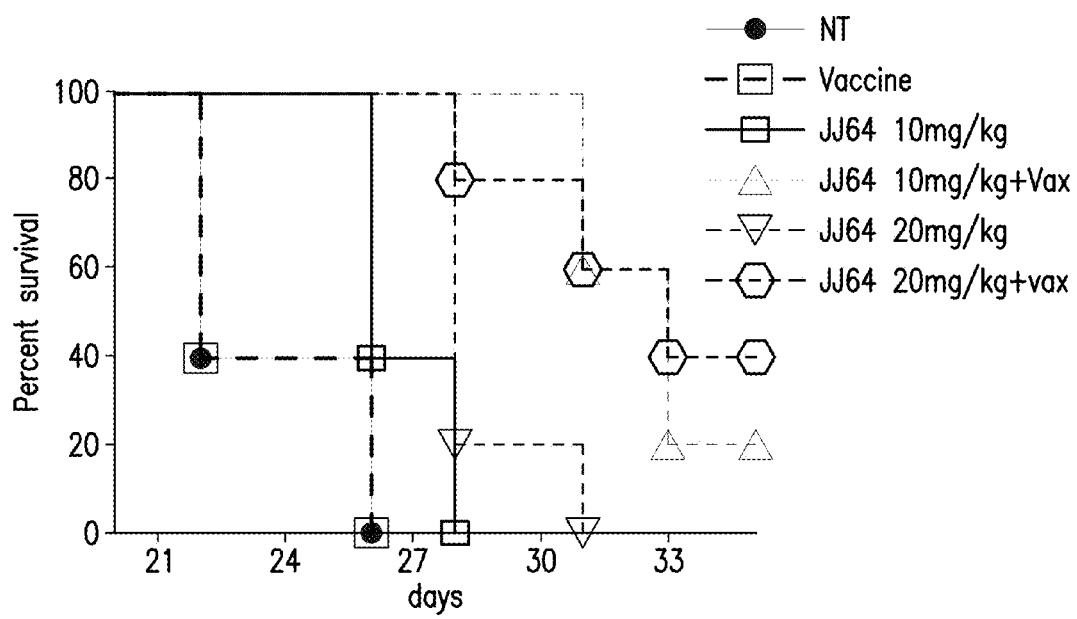
FIG. 5D

SPECIFIC AKT3 INHIBITOR AND USES THEREOF

CROSS-REFERENCE TO RELATED APPLICATIONS

This application claims benefit of and priority to U.S. Provisional Patent Application No. 62/279,248 filed on Jan. 15, 2016, and is incorporated by reference in its entirety.

REFERENCE TO SEQUENCE LISTING

The Sequence Listing submitted Jan. 17, 2017, as a text file named "016_ST25.txt" created on Jan. 17, 2017, and having a size of 11 Kilo bytes is hereby incorporated by reference pursuant to 37 C.F.R. § 1.52(e)(5).

FIELD OF THE INVENTION

The invention is generally directed to compositions and methods for selective inhibition of Akt3 activity, and methods of use thereof for modulating regulator T cells.

BACKGROUND OF THE INVENTION

Regulatory T cells (Tregs) are a subset of CD4+ T cells that suppress immune responses and are essential mediators of self-tolerance and immune homeostasis (Sakaguchi, et al., Cell, 133, 775-787 (2008)). Depletion or inactivation of Tregs results in the development of severe autoimmunity (Sakaguchi, et al., J. Immunol., 155, 1151-1164 (1995)), and their accumulation inhibits anti-tumor immunity (Dannull, et al., The Journal of clinical investigation, 115, 3623-3633 (2005)). Tregs are characterized by Foxp3 expression, a transcription factor belonging to the Forkehead Box family of transcription factors. The Foxp3 is a master regulator of Tregs, as it is necessary for their development and function (Hori, Science, 299, 1057-1061 (2003); Fontenot, et al., Nat Immunol., 4(4):330-6 (2003). Epub 2003 Mar. 3; Khattri, et al., Nat Immunol., 4(4):337-42 (2003). Epub 2003 Mar. 3)).

There are two major types of Tregs: thymus-derived Tregs (or natural Tregs (nTregs)) that constitute 5-10% of the total peripheral CD4+ T cells, and peripheral TGFβ-induced Tregs (iTregs). Both types are shown to have immunosuppressive properties mediated via several processes that involve immunosuppressive soluble factors or cell contact (Bluestone, et al., Nat Rev Immunol, 3, 253-257 (2003); Glisic, et al., Cell and Tissue Research, 339, 585-595 (2010); Hori, Science, 299, 1057-1061 (2003); Sakaguchi, Cell, 101, 455-458 (2000); Sakagushi, et al., Curr. Top Microbiol. Immunol., 305, 51-66 (2006); Sakagushi, et al., Immunol., Rev., 212, 8-27 (2006); (Schmidt, et al., Front Immunol., 3:51 (2012)). However, the molecular mechanisms by which nTreg and iTreg develop and then exhibit non-redundant roles to suppress the immunity are not fully understood (Dipica, et al., Immunity, 35(1):109-122 (2011)).

PI3K-Akt signaling affects many processes and is central to many signaling pathways. Akt phosphorylation and kinase activity are induced by PI3K activation, which is, in turn, induced by several growth factor receptors, TCR, CD28, and IL-2R, among many others (Parry, et al., Trends in Immunology, 28, 161-168 (2007)). In mammals, there are three Akt isoforms, namely Akt1, Akt2, and Akt3, encoded by three independent genes. In vitro, these isoforms appear to have redundant functions, as different extracellular inputs can induce similar Akt signaling patterns (Franke, Science 1, pe29-(2008)). However, isoform-specific knockouts show unique features and their involvement in diseases and physiological conditions is different (Boland, et al., American Journal of Human Genetics, 81, 292-303 (2007); DeBosch, et al., J. Biol. Chem, 281, 32841-32851 (2006); Emamian, et al., Nat Genet, 36, 131-137 (2004); Garofalo, et al., The Journal of clinical investigation, 112, 197-208 (2003); George, et al., Science, 304, 1325-1328 (2004); Nakatani, et al., The Journal of Biological Chemistry, 274, 21528-21532 (1999); Tschopp, et al., Development (Cambridge, England), 132, 2943-2954 (2005); Yang, et al., J. Biol. Chem., 278, 32124-32131 (2003)).

Studies have shown that Akt1 and Akt2 can negatively regulate the transcriptional signature of Treg, thereby selectively affecting Treg lineage differentiation (Sauer, et al., Proceedings of the National Academy of Sciences, 105, 7797-7802 (2008a)). Additionally, although it was shown that inhibition of Akt1 and Akt2 isoforms increase Foxp3 expression in TGFβ induced iTregs (Sauer, et al., Proc. Natl. Acad. Sci. USA, 105, 7797-7802 (2008b)), the mechanism remained unclear. Another finding shows that deletion of Akt2 resulted in defective iTh17 cell differentiation but preserved nTh17 cell development (Kim, et al., Nat Immunol., 14(6):611-8 (2013) Epub 2013 May 5). Further, Akt3 is also expressed in immune cells and the spinal cord of Akt3 knockout mice have decreased numbers of Foxp3+ regulatory T cells compared with wild type mice (Tsiperson, et al., J Immunol., 190(4):1528-39 (2013) Epub 2013 Jan. 18)). Thus, although some studies have examined the relevance of Akt isoform expression on T cell biology (Carson, et al., Annals of the New York Academy of Sciences, 1103, 167-178 (2007), Crellin, et al., Blood, 109, 2014-2022 (2007a); Crellin, et al., Journal of Immunological Methods, 324, 92-104 (2007b); Haxhinasto, J. Exp. Med., 205, 565-574 (2008); Li, et al., Blood, 106, 3068-3073 (2005); Patton, et al., Biochem. Soc. Trans., 35, 167-171 (2007); Patton, et al., J. Immunology 177, 6598-6602 (2006); Sauer, et al., Proc. Natl. Acad. Sci. USA, 105, 7797-7802 (2008b); Walsh, et al., J. Clin. Invest., 116, 2521-2531. (2006)), the roles that Akt isoforms play in Treg function and induction was not clear.

Therefore, it is an object of the invention to provide compounds and compositions for selectively inhibiting Akt3 in a subject.

It is another object of the invention to provide methods of increasing a stimulatory immune response in a subject.

Still another object of the invention is to provide methods of decreasing a suppressive immune response in a subject.

SUMMARY OF THE INVENTION

Methods of selectively inhibiting Akt3 are provided. It has been discovered that 4-[(6-nitroquinolin-4-yl)amino]-N-[4-(pyridin-4-ylamino)phenyl]benzamide selectively inhibits Akt3. Because Akt3 modulates the suppressive function of natural Tregs and the polarization of induced Tregs, 4-[(6-nitroquinolin-4-yl)amino]-N-[4-(pyridin-4-ylamino) phenyl]benzamide can be used for modulating immune responses.

For example, methods of decreasing an immune suppressive response, increasing an immune stimulating response, or a combination thereof in a subject in need thereof are disclosed. The methods typically include administering the subject a composition including 4-[(6-nitroquinolin-4-yl)amino]-N-[4-(pyridin-4-ylamino)phenyl]benzamide that selectively inhibits the bioactivity of Akt3 in an amount effective to reduce the immune suppressive response, increase the immune stimulating response, or a combination thereof in the subject.

In some embodiments the immune suppressive response that is reduced is selected from the group consisting of an immune suppressive function of natural Treg (nTreg) and induction of conventional T cells into induced Treg (iTreg). The immune suppressive function of nTreg can be the secretion of one or more anti-inflammatory cytokines. The anti-inflammatory cytokine(s) can IL10, TGFβ, or a combination thereof.

In some embodiments, the subject has cancer or an infection. Therefore, methods of treating cancers and infections by administering a subject in need thereof an effective amount of a compound that reduces the bioavailability of Akt3 are also disclosed. Exemplary cancers that can be treated include, but are not limited to, bladder, brain, breast, cervical, colo-rectal, esophageal, kidney, liver, lung, nasopharangeal, pancreatic, prostate, skin, stomach, uterine, ovarian, testicular and hematologic cancers. Exemplary infectious diseases that can be treated include, but are not limited to, those caused by a bacterium, virus, protozoan, helminth, or another microbial pathogen.

Combination therapies and vaccine formulations including modulators of Akt3 bioactivity and methods of use thereof are also provided.

BRIEF DESCRIPTION OF THE DRAWINGS

FIGS. 3B-3J are histograms of FACS sorted cells from mice as treated in FIG. 3A.

FIGS. 4B-4J are dot plots of flow cytometry analysis of animals treated with 5 mg/kg or 10 mg/kg of 4-[(6-nitroquinolin-4-yl)amino]-N-[4-(pyridin-4-ylamino)phenyl]benzamide. FIG. 4K is a bar graph of CD4+ T cells (% of CD3) for animals treated with 5 mg/kg or 10 mg·kg of 4-[(6-nitroquinolin-4-yl)amino]-N-[4-(pyridin-4-ylamino)phenyl]benzamide. FIG. 4L is a bar graph of CD8+ T cells (% of CD3) for animals treated with 5 mg/kg or 10 mg·kg of 4-[(6-nitroquinolin-4-yl)amino]-N-[4-(pyridin-4-ylamino)phenyl]benzamide.

FIG. 5A is a schematic of treatment regimen. FIG. 5B is a bar graph of Tumor volume ($cm^3$) for from left to right, untreated, vaccine, 10 mg/kg 4-[(6-nitroquinolin-4-yl)amino]-N-[4-(pyridin-4-ylamino)phenyl]benzamide, and 10 mg/kg of 4-[(6-nitroquinolin-4-yl)amino]-N-[4-(pyridin-4-ylamino)phenyl]benzamide with vaccine. FIG. 5C is a bar graph of Tumor volume (cm3) for from left to right, untreated, vaccine, 20 mg/kg 4-[(6-nitroquinolin-4-yl)amino]-N-[4-(pyridin-4-ylamino)phenyl]benzamide, and 20 mg/kg of 4-[(6-nitroquinolin-4-yl)amino]-N-[4-(pyridin-4-ylamino)phenyl]benzamide with vaccine. FIG. 5D is a Kaplan-Meier plot of the overall survival.

DETAILED DESCRIPTION OF THE INVENTION

I. Definitions

Figure 1:
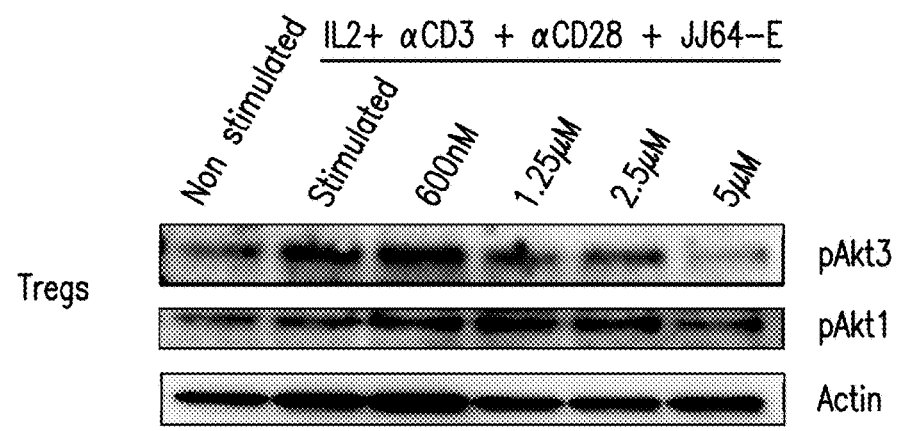
FIG. 1 is an autoradiograph of an immunoblot of Tregs treated as indicated with 4-[(6-nitroquinolin-4-yl)amino]-N-[4-(pyridin-4-ylamino)phenyl]benzamide and assayed for phosphorylation of pAkt3, pAkt1, or Actin.
Figure 2A:
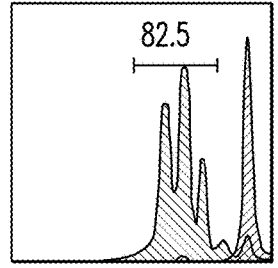
FIGS. 2A-2P are histograms of FACS sorted nTregs treated as indicated with 4-[(6-nitroquinolin-4-yl)amino]-N-[4-(pyridin-4-ylamino)phenyl]benzamide.
Figure 2B:
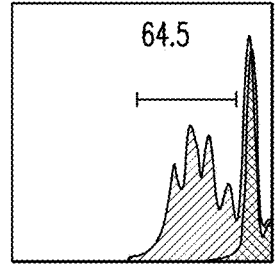
Figure 2C:
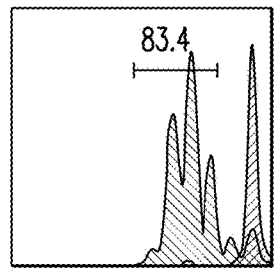
Figure 2D:
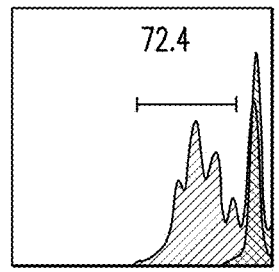
Figure 2E:
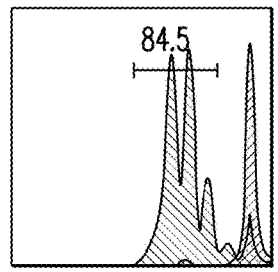
Figure 2F:
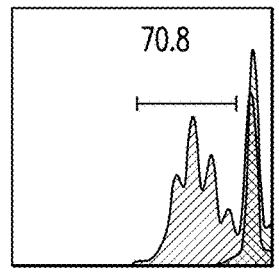
Figure 2G:
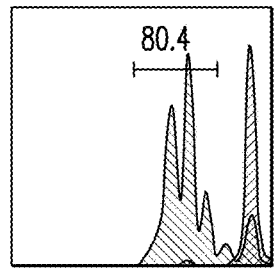
Figure 2H:
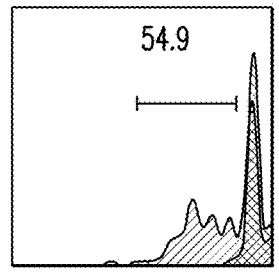
Figure 3A:
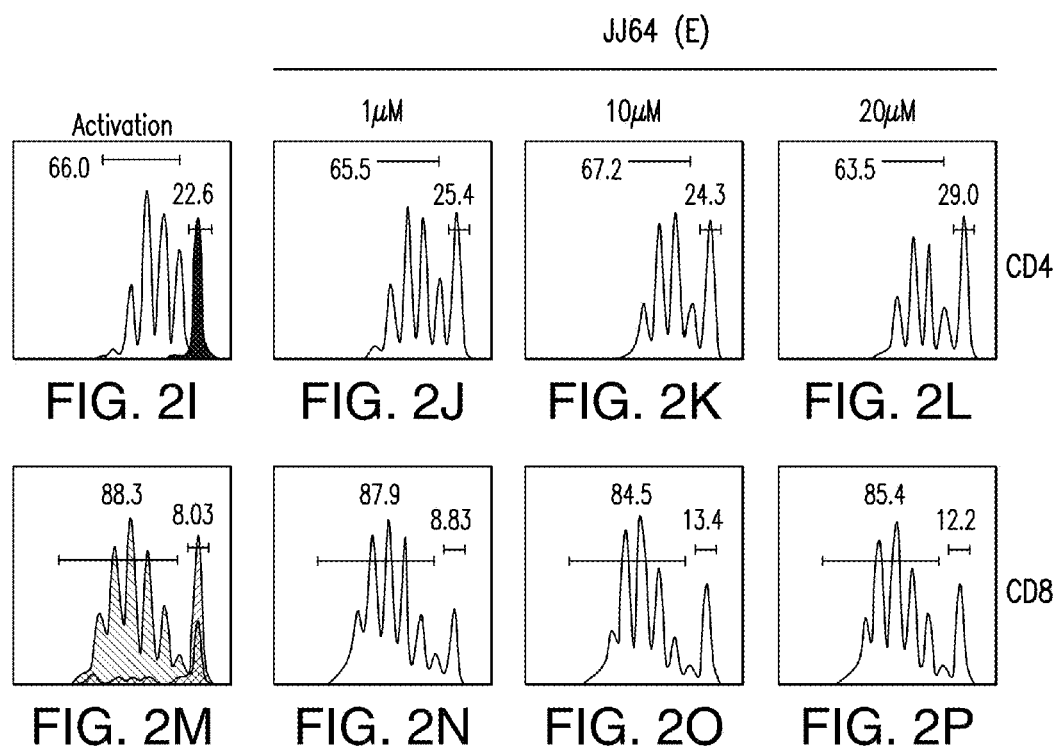
FIG. 3A is a schematic of a treatment regimen with 4-[(6-nitroquinolin-4-yl)amino]-N-[4-(pyridin-4-ylamino)phenyl]benzamide.
Figure 3A:
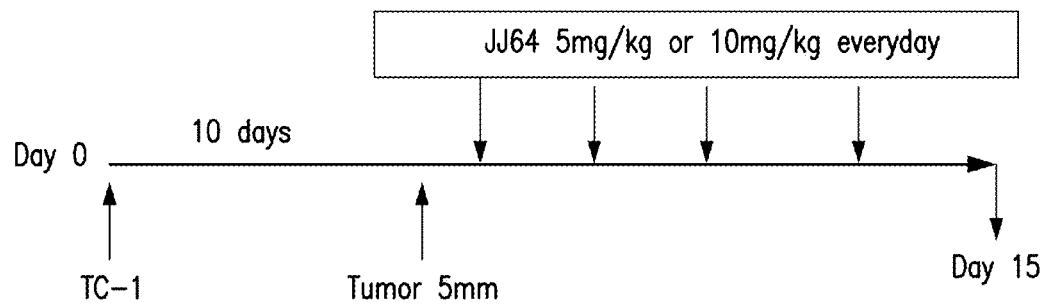
Figure 3K:
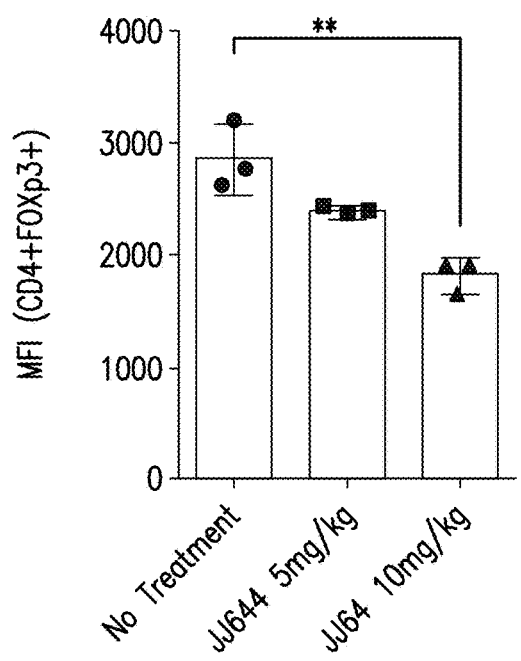
FIG. 3K is a bar graph of MFI (CD4+FOXp3+) from animals treated with 5 mg/kg or 10 mg/kg 4-[(6-nitroquinolin-4-yl)amino]-N-[4-(pyridin-4-ylamino)phenyl]benzamide.
Figure 3L:
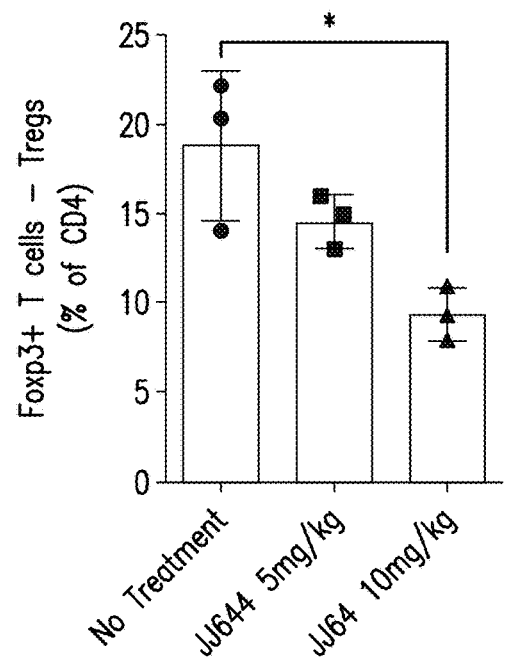
FIG. 3L is a bar graph of Foxp3+ Tcells–Tregs (% of CD4) of animals treated with 5 mg/kg or 10 mg/kg of 4-[(6-nitroquinolin-4-yl)amino]-N-[4-(pyridin-4-ylamino)phenyl]benzamide.
Figure 4A:
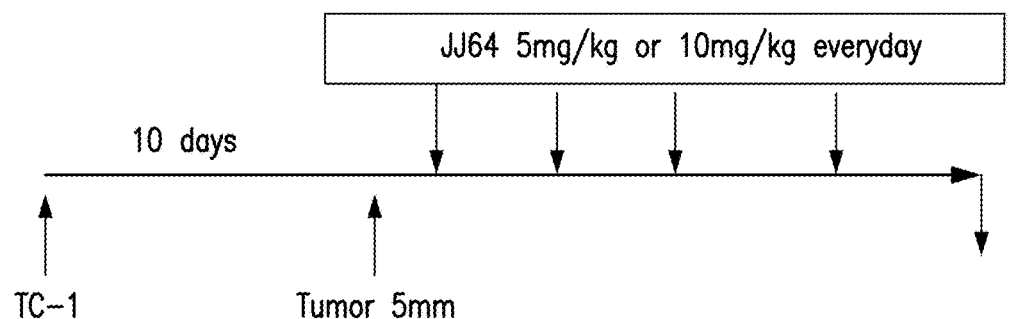
FIG. 4A is a schematic of a treatment regimen.

The term "stimulate expression of" means to affect expression of, for example to induce expression or activity, or induce increased/greater expression or activity relative to normal, healthy controls.

The terms "immune activating response", "activating immune response", and "immune stimulating response" refer to a response that initiates, induces, enhances, or increases the activation or efficiency of innate or adaptive immunity. Such immune responses include, for example, the development of a beneficial humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells and/or $CD8^+$ cytotoxic T cells. The response can also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

The terms "suppressive immune response" and "immune suppressive response" refer to a response that reduces or prevents the activation or efficiency of innate or adaptive immunity.

The term "immune tolerance" as used herein refers to any mechanism by which a potentially injurious immune response is prevented, suppressed, or shifted to a non-injurious immune response (Bach, et al., *N. Eng. J. Med.*, 347:911-920 (2002)).

The term "tolerizing vaccine" as used herein is typically an antigen-specific therapy used to attenuate autoreactive T and/or B cell responses, while leaving global immune function intact.

An "immunogenic agent" or "immunogen" is capable of inducing an immunological response against itself on administration to a mammal, optionally in conjunction with an adjuvant.

The term "immune cell" refers to cells of the innate and acquired immune system including neutrophils, eosinophils, basophils, monocytes, macrophages, dendritic cells, lymphocytes including B cells, T cells, and natural killer cells.

As used herein "conventional T cells" are T lymphocytes that express an αβ T cell receptor (TCR) as well as a co-receptor CD4 or CD8. Conventional T cells are present in the peripheral blood, lymph nodes, and tissues. See, Roberts and Girardi, "Conventional and Unconventional T Cells", *Clinical and Basic Immunodermatology*, pp. 85-104, (Gaspari and Tyring (ed.)), Springer London (2008).

As used herein "unconventional T cells" are lymphocytes that express a γδ TCR and may commonly reside in an epithelial environment such as the skin, gastrointestinal tract, or genitourinary tract. Another subset of unconventional T cells is the invariant natural killer T (NKT) cell, which has phenotypic and functional capacities of a conventional T cell, as well as features of natural killer cells (e.g., cytolytic activity). See, Roberts and Girardi, "Conventional and Unconventional T Cells", *Clinical and Basic Immunodermatology*, pp. 85-104, (Gaspari and Tyring (ed.)), Springer London (2008).

As used herein "Treg" refers to a regulatory T cell or cells. Regulatory T cells are a subpopulation of T cells which modulate the immune system, maintain tolerance to self-antigens, abrogate autoimmune disease, and otherwise suppress immune stimulating or activating responses of other cells. Regulatory T cells come in many forms with the most well-understood being those that express CD4, CD25, and Foxp3.

As used herein "natural Treg" or "nTreg" refers to a regulatory T cell or cells that develop in the thymus.

As used herein "induced Treg" or "iTreg" refers to a regulatory T cell or cells that develop from mature CD4+ conventional T cells outside of the thymus.

The "bioactivity" of Akt3 refers to the biological function of the Akt3 polypeptide. Bioactivity can be increased or reduced by increasing or reducing the activity of basal levels of polypeptide, increasing or reducing the avidity of basal levels of polypeptide, the quantity of the polypeptide, the ratio of Akt3 relative to one or more other isoforms of Akt (e.g., Akt1 or Akt2) of the polypeptide, increasing or reducing the expression levels of the polypeptide (including by increasing or decreasing mRNA expression of Akt3), or a combination thereof. For example, bioavailable Akt3 polypeptide is a polypeptide that has kinase activity and can bind to and phosphorylate a substrate of Akt3. Akt3 polypeptide that is not bioavailable includes Akt3 polypeptide that is mis-localized or in-capable of binding to and phosphorylating Akt substrates.

As used herein, the phrase that a molecule "specifically binds" or "displays specific binding" to a target refers to a binding reaction which is determinative of the presence of the molecule in the presence of a heterogeneous population of other biologics.

Under designated immunoassay conditions, a specified molecule binds preferentially to a particular target and does not bind in a significant amount to other biologics present in the sample. Specific binding of an antibody to a target under such conditions requires the antibody be selected for its specificity to the target. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The terms "oligonucleotide" and "polynucleotide" generally refer to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "carrier" refers to an organic or inorganic ingredient, natural or synthetic, with which the active ingredient is combined to facilitate the application.

The term "pharmaceutically acceptable" means a non-toxic material that does not interfere with the effectiveness of the biological activity of the active ingredients.

The term "pharmaceutically-acceptable carrier" means one or more compatible solid or liquid fillers, dilutants or encapsulating substances which are suitable for administration to a human or other vertebrate animal.

The term "effective amount" or "therapeutically effective amount" means a dosage sufficient to provide treatment a disorder, disease, or condition being treated, or to otherwise provide a desired pharmacologic and/or physiologic effect. The precise dosage will vary according to a variety of factors such as subject-dependent variables (e.g., age, immune system health, etc.), the disease, and the treatment being effected.

The terms "individual," "individual," "subject," and "patient" are used interchangeably herein, and refer to a mammal, including, but not limited to, humans, rodents, such as mice and rats, and other laboratory animals.

II. Compositions for Inhibiting Akt3

It has been discovered that 4-[(6-nitroquinolin-4-yl)amino]-N-[4-(pyridin-4-ylamino)phenyl]benzamide selectively inhibits Akt3 activity. 4-[(6-nitroquinolin-4-yl)amino]-N-[4-(pyridin-4-ylamino)phenyl]benzamide has CAS No. 50440-30-7 and the following chemical structure:

Formula I

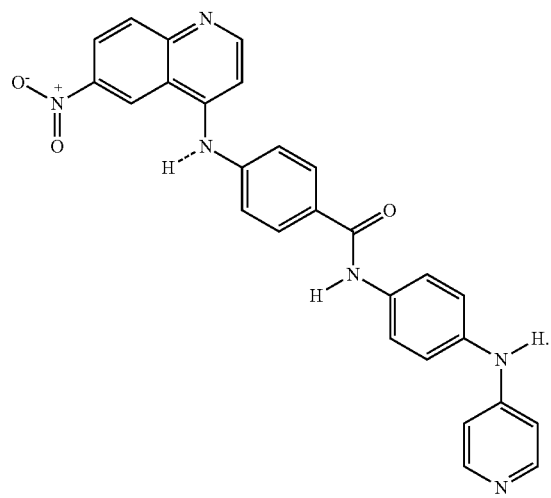

Other compounds for selectively inhibiting Akt3 that can be used in combination or alternation with 4-[(6-nitroquinolin-4-yl)amino]-N-[4-(pyridin-4-ylamino)phenyl]benzamide include the following:

(1)

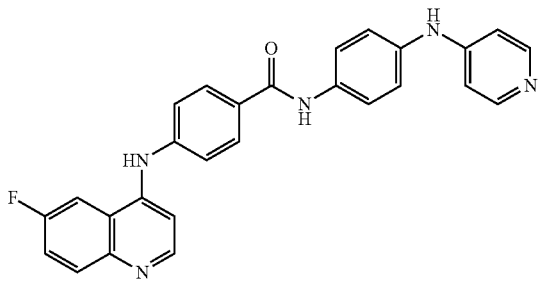

(2)

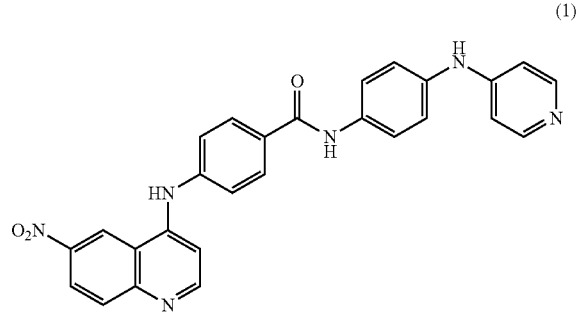

(3)

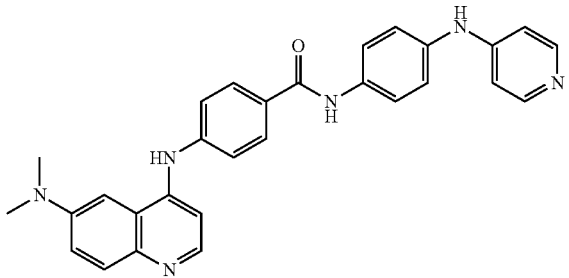

(4)

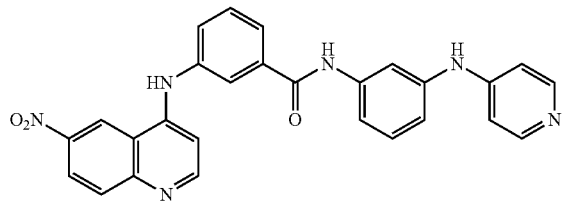

(5)

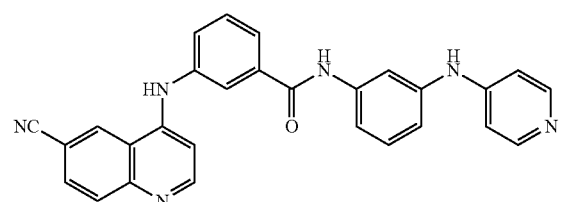

(6)

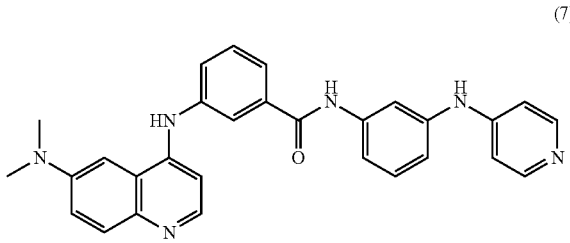

(7)

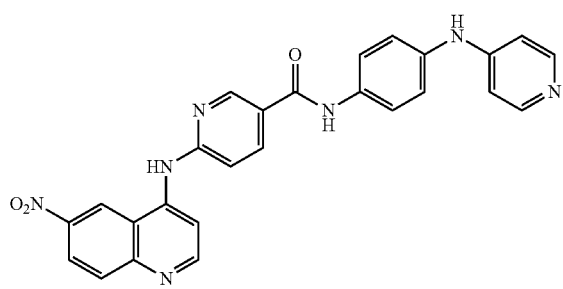

(8)

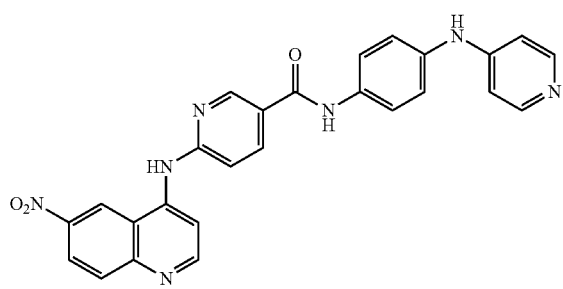

-continued
(9)
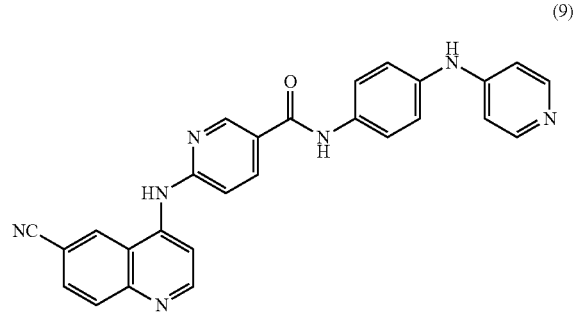
(10)
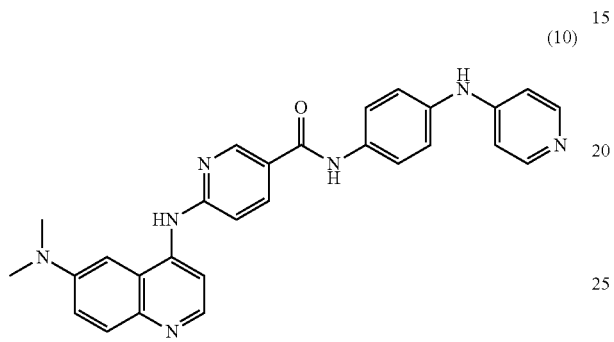
(11)
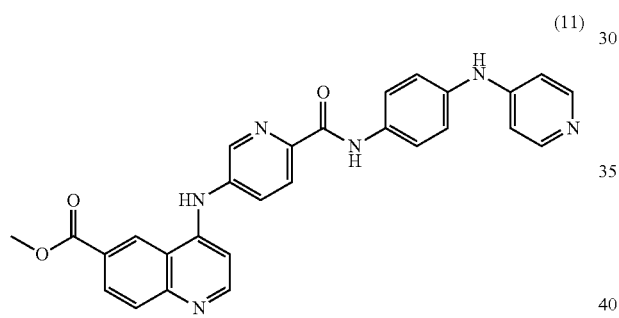
(12)
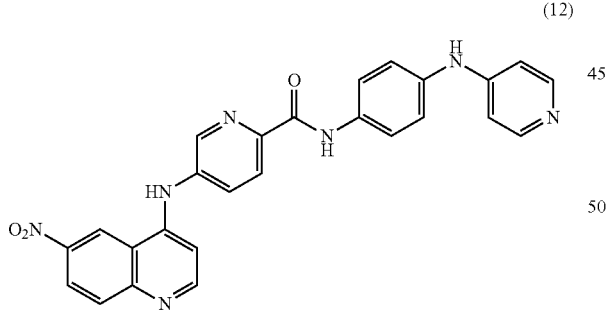
(13)
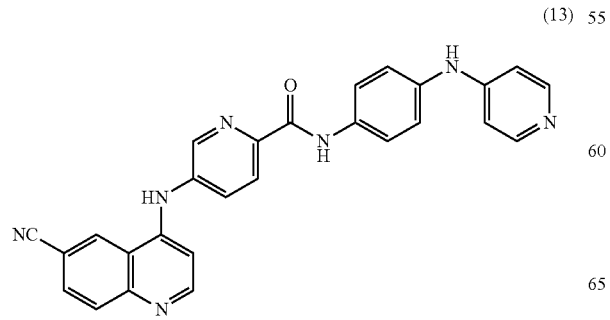
-continued
(14)
(15)
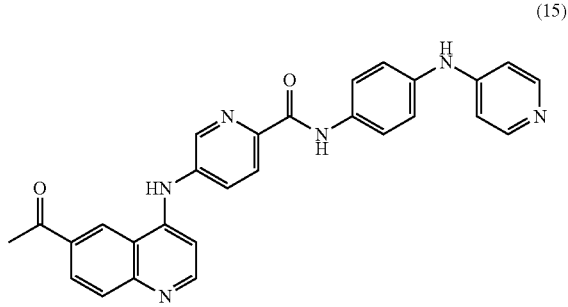
(16)
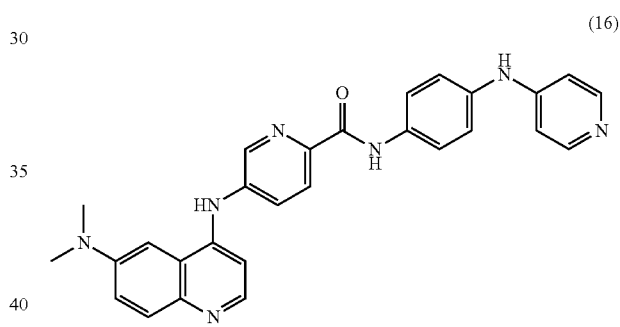
(17)
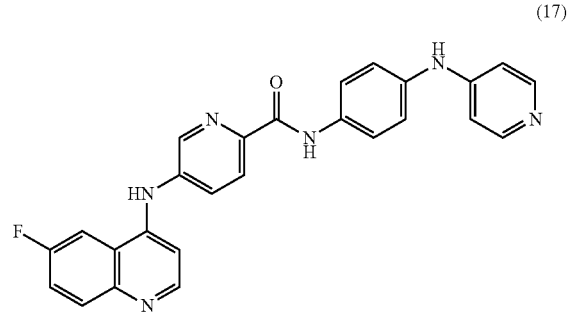
(18)
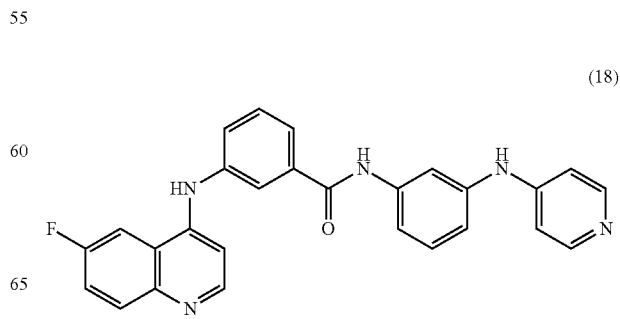

-continued

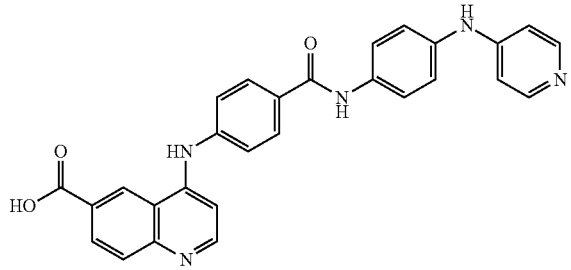
(19)

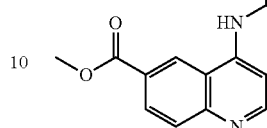
(25)

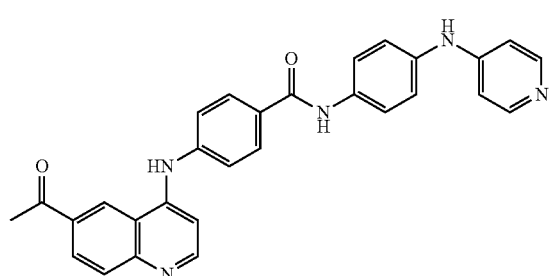
(20)

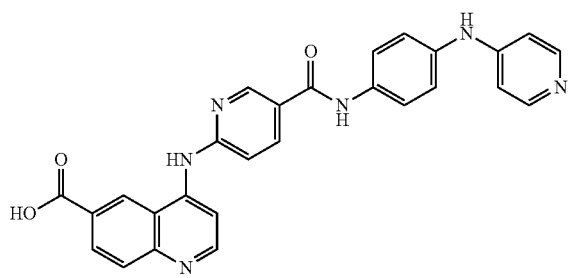
(26)

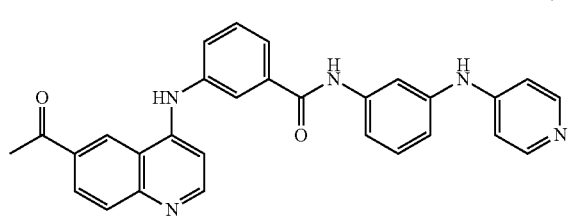
(21)

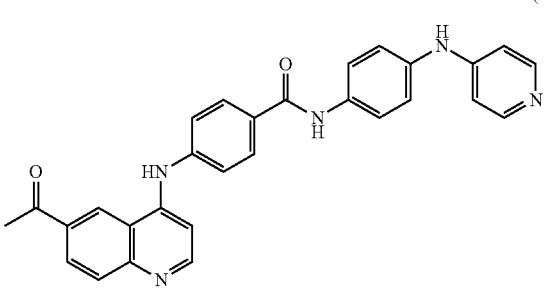
(27)

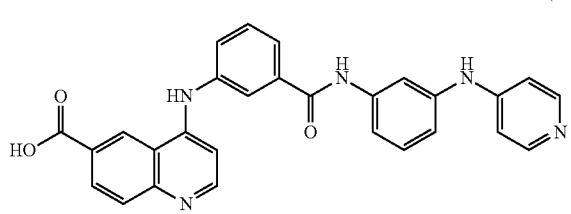
(22)

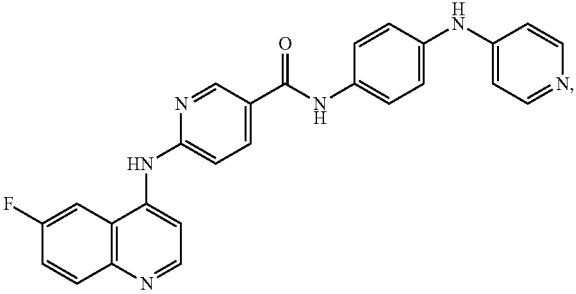
(28)

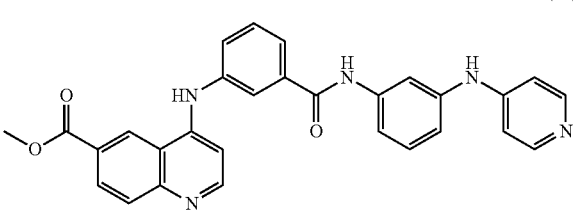
(23)

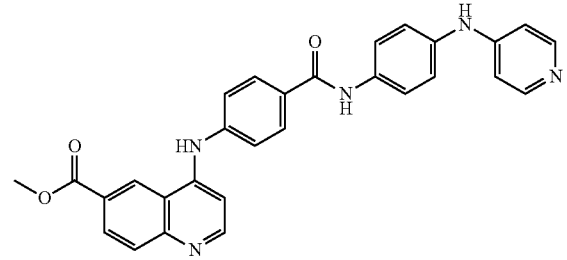
(24)

and enantiomers, polymorphs, pharmaceutically acceptable salts, and derivatives thereof. As used herein, "compounds 1-28" refers to any one or combination of 2 or more of compounds 1-28, and enantiomers, polymorphs, pharmaceutically acceptable salts and derivatives thereof.

In some embodiments, the Atk3 inhibitor is a derivative of Formula I and any one of compounds 1-28. The term "derivative" or "derivatised" as used herein includes one or more chemical modifications of Formula I and any one of compounds 1-28, an enantiomer, polymorph, or pharmaceutically acceptable salt thereof. That is, a "derivative" may be a functional equivalent of Formula I and any one of compounds 1-28, which is capable of inducing the improved pharmacological functional activity and/or behavioral response in a given subject. Illustrative of such chemical modifications would be replacement of hydrogen by a halo group, an alkyl group, an acyl group or an amino group.

The chemical modification of Formula I and any one of compounds 1-28, an enantiomer, polymorph, or pharmaceutically acceptable salt thereof may either enhance or reduce hydrogen bonding interaction, charge interaction, hydrophobic interaction, Van Der Waals interaction or dipole interaction between the compound and its target.

In some embodiments, the compound of Formula I and any one of compounds 1-28 may act as a model (for example, a template) for the development of other derivative compounds which are a functional equivalent of the compound and which is capable of inducing the improved pharmacological functional activity and/or effect and/or behavioral response in a given subject.

Compounds Formula I and 1-28 may be racemic compounds and/or optically active isomers thereof. In this regard, some of the compounds can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer(s).

Compounds of Formula I and 1-28 selectively inhibit Akt3 compared to Akt1 and Akt2. In certain embodiments, compounds 1-28 do not inhibit Akt1 and Akt2 to a statistically significant degree. In other embodiments, inhibition of Akt3 by compounds 1-28 is 5, 10, 15, 50, 100, 1000, or 5000 fold greater than their inhibition of Akt1 and Akt2.

Akt3, also referred to as RAC-gamma serine/threonine-protein kinase is an enzyme that in humans is encoded by the Akt3 gene. Akt kinases are known to be regulators of cell signaling in response to insulin and growth factors and are associated with a broad range of biological processes including cell proliferation, differentiation, apoptosis, tumorigenesis, as well as glycogen synthesis and glucose uptake. Akt3 has been shown to be stimulated by platelet-derived growth factor (PDGF), insulin, and insulin-like growth factor 1 (IGF1).

Akt3 kinase activity mediates serine and/or threonine phosphorylation of a range of downstream substrates. Nucleic acid sequences for Akt3 are known in the art. See, for example, Genbank accession no. AF124141.1: *Homo sapiens* protein kinase B gamma mRNA, complete cds, which is specifically incorporated by references in its entirety, and provides the nucleic acid sequence:

(SEQ ID NO: 1)
AGGGGAGTCATCATGAGCGATGTTACCATTGTGAAGGAAGGTTGGGTTCA

GAAGAGGGGAGAATATATAAAAAACTGGAGGCCAAGATACTTCCTTTTGA

AGACAGATGGCTCATTCATAGGATATAAAGAGAAACCTCAAGATGTGGAT

-continued
TTACCTTATCCCCTCAACAACTTTTCAGTGGCAAAATGCCAGTTAATGAA

AACAGAACGACCAAAGCCAAACACATTTATAATCAGATGTCTCCAGTGGA

CTACTGTTATAGAGAGAACATTTCATGTAGATACTCCAGAGGAAAGGGAA

GAATGGACAGAAGCTATCCAGGCTGTAGCAGACAGACTGCAGAGGCAAGA

AGAGGAGAGAATGAATTGTAGTCCAACTTCACAAATTGATAATATAGGAG

AGGAAGAGATGGATGCCTCTACAACCCATCATAAAAGAAAGACAATGAAT

GATTTTGACTATTTGAAACTACTAGGTAAAGGCACTTTTGGGAAAGTTAT

TTTGGTTCGAGAGAAGGCAAGTGGAAAATACTATGCTATGAAGATTCTGA

AGAAAGAAGTCATTATTGCAAAGGATGAAGTGGCACACACTCTAACTGAA

AGCAGAGTATTAAAGAACACTAGACATCCCTTTTTAACATCCTTGAAATA

TTCCTTCCAGACAAAAGACCGTTTGTGTTTTGTGATGGAATATGTTAATG

GGGGCGAGCTGTTTTTCCATTTGTCGAGAGAGCGGGTGTTCTCTGAGGAC

CGCACACGTTTCTATGGTGCAGAAATTGTCTCTGCCTTGGACTATCTACA

TTCCGGAAAGATTGTGTACCGTGATCTCAAGTTGGAGAATCTAATGCTGG

ACAAAGATGGCCACATAAAAATTACAGATTTTGGACTTTGCAAAGAAGGG

ATCACAGATGCAGCCACCATGAAGACATTCTGTGGCACTCCAGAATATCT

GGCACCAGAGGTGTTAGAAGATAATGACTATGGCCGAGCAGTAGACTGGT

GGGGCCTAGGGGTTGTCATGTATGAAATGATGTGTGGGAGGTTACCTTTC

TACAACCAGGACCATGAGAAACTTTTTGAATTAATATTAATGGAAGACAT

TAAATTTCCTCGAACACTCTCTTCAGATGCAAAATCATTGCTTTCAGGGC

TCTTGATAAAGGATCCAAATAAACGCCTTGGTGGAGGACCAGATGATGCA

AAAGAAATTATGAGACACAGTTTCTTCTCTGGAGTAAACTGGCAAGATGT

ATATGATAAAAAGCTTGTACCTCCTTTTAAACCTCAAGTAACATCTGAGA

CAGATACTAGATATTTTGATGAAGAATTTACAGCTCAGACTATTACAATA

ACACCACCTGAAAAATATGATGAGGATGGTATGGACTGCATGGACAATGA

GAGGCGGCCGCATTTCCCTCAATTTTCCTACTCTGCAAGTGGACGAGAAT

AAGTCTCTTTCATTCTGCTACTTCACTGTCATCTTCAATTTATTACTGAA

AATGATTCCTGGACATCACCAGTCCTAGCTCTTACACATAGCAGGGCAC

CTTCCGACATCCCAGACCAGCCAAGGGTCCTCACCCCTCGCCACCTTTCA

CCCTCATGAAAACACACATACACGCAAATACACTCCAGTTTTTGTTTTTG

CATGAAATTGTATCTCAGTCTAAGGTCTCATGCTGTTGCTGCTACTGTCT

TACTATTA.

Amino acid sequences are also known in the art. See, for example, UniProtKB/Swiss-Prot accession no. Q9Y243 (Akt3_HUMAN), which is specifically incorporated by reference in its entirety and provides the amino acid sequence:

(SEQ ID NO: 2)
MSDVTIVKEGWVQKRGEYIKNWRPRYFLLKTDGSFIGYKEKPQDVDLPYP

LNNFSVAKCQLMKTERPKPNTFIIRCLQWTTVIERTFHVDTPEEREEWTE

ATQAVADRLQRQEEERMNCSPTSQIDNIGEEEMDASTTHHKRKTMNDFDY

LKLLGKGTFGKVILVREKASGKYYAMKILKKEVIIAKDEVAHTLTESRVL

KNTRHPFLTSLKYSFQTKDRLCFVMEYVNGGELFFHLSRERVFSEDRTRF

-continued
YGAEIVSALDYLHSGKIVYRDLKLENLMLDKDGHIKITDFGLCKEGITDA

ATMKTFCGTPEYLAPEVLEDNDYGRAVDWWGLGVVMYEMMCGRLPFYNQD

HEKLFELILMEDIKFPRTLSSDAKSLLSGLLIKDPNKRLGGGPDDAKEIM

RHSFESGVNWQDVYDKKLVPPFKPQVTSETDTRYFDEEFTAQTITITPPE

KYDEDGMDCMDNERRPHFPQFSYSASGRE.

The domain structure of Akt3 is reviewed in Romano, Scientifica, Volume 2013 (2013), Article ID 317186, 12 pages, and includes an N-terminal pleckstrin homology domain (PH), followed by a catalytic kinase domain (KD), and the C-terminal regulatory hydrophobic region. The catalytic and regulatory domains are both important for the biological actions mediated by Akt protein kinases and exhibit the maximum degree of homology among the three Akt isoforms. The PH domain binds lipid substrates, such as phosphatidylinositol (3,4) diphosphate (PIP2) and phosphatidylinositol (3,4,5) triphosphate (PIP3). The ATP binding site is situated approximately in the middle of the catalytic kinase domain, which has a substantial degree of homology with the other components of the AGCkinases family, such as p70 S6 kinase (S6K) and p90 ribosomal S6 kinase (RSK), protein kinase A (PKA) and protein kinase B (PKB). The hydrophobic regulatory moiety is a typical feature of the AGC kinases family. With reference to SEQ ID NO:2, Akt 3 is generally considered to have the following molecule processing and domain structure outlined below.

Molecule Processing:

| Feature key | Position(s) | Length | Description |
| --- | --- | --- | --- |
| Initiator methionine | 1 | 1 | Removed |
| Chain | 2-479 | 478 | Akt3 |

Regions:

| Feature key | Position(s) | Length | Description |
| --- | --- | --- | --- |
| Domain | 5-107 | 103 | PH |
| Domain | 148-405 | 258 | Protein kinase |
| Domain | 406-479 | 74 | AGC-kinase C-terminal |
| Nucleotide binding | 154-162 | 9 | ATP |

Sites:

| Feature key | Position(s) | Length | Description |
| --- | --- | --- | --- |
| Active site | 271 | 1 | Proton acceptor |
| Binding site | 177 | 1 | ATP |

The initiator methionine of SEQ ID NO:2 is disposable for Akt3 function. Therefore, in some embodiments, the compound directly or indirectly inhibits expression or bioavailability of an Akt3 having the amino acid sequence (SEQ ID NO: 3)
SDVTIVKEGWVQKRGEYIKNWRPRYFLLKTDGSFIGYKEKPQDVDLPYPL

NNFSVAKCQLMKTERPKPNTFIIRCLQWTTVIERTFHVDTPEEREEWTEA

TQAVADRLQRQEEERMNCSPTSQIDNIGEEEMDASTTHHKRKTMNDFDYL

KLLGKGTFGKVILVREKASGKYYAMKILKKEVIIAKDEVAHTLTESRVLK

-continued
NTRHPFLTSLKYSFQTKDRLCFVMEYVNGGELFFHLSRERVFSEDRTRFY

GAEIVSALDYLHSGKIVYRDLKLENLMLDKDGHIKITDFGLCKEGITDAA

TMKTFCGTPEYLAPEVLEDNDYGRAVDWWGLGVVMYEMMCGRLPFYNQDH

EKLFELILMEDIKEPRTLSSDAKSLLSGLLIKDPNKRLGGGPDDAKEIMR

HSFFSGVNWQDVYDKKLVPPFKPQVTSETDTRYFDEEFTAQTITITPPEK

YDEDGMDCMDNERRPHFPQFSYSASGRE.

Two specific sites, one in the kinase domain (Thr-305 with reference to SEQ ID NO:2) and the other in the C-terminal regulatory region (Ser-472 with reference to SEQ ID NO:2), need to be phosphorylated for full activation of Akt3. Interaction between the PH domain of Akt3 and TCL1A enhances Akt3 phosphorylation and activation. IGF-1 leads to the activation of Akt3, which may play a role in regulating cell survival.

Compounds 1-28 can inhibit Akt3 activity by binding to one or more active sites on the Akt3 polypeptide. A preferred binding site is one or both of the kinase domains.

A. Formulations

Another embodiment provides formulations of and pharmaceutical compositions including one or more of compounds of Formula I and any one or more of compounds 1-28 are provided. Generally, dosage levels, for the compounds disclosed herein are between about 0.0001 mg/kg of body weight to about 1,000 mg/kg, more preferably of 0.001 to 500 mg/kg, more preferably 0.01 to 50 mg/kg of body weight daily are administered to mammals.

1. Delivery Vehicles

4-[(6-nitroquinolin-4-yl)amino]-N-[4-(pyridin-4-ylamino)phenyl]benzamide (also referred to as Formula I) and compounds 1-28 can be administered to a subject, preferably a human subject, where it is taken up into the cells of a subject with or without the aid of a delivery vehicle. Appropriate delivery vehicles for the disclosed active agents are known in the art and can be selected to suit the particular active agent. For example, in some embodiments, the compound is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

The compounds can be incorporated into a delivery vehicle prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

Pharmaceutical compositions including Formula I and optionally compounds 1-28, with or without a delivery vehicle, are provided. Pharmaceutical compositions can be formulated for administration by parenteral (intramuscular, intraperitoneal, intravenous (IV) or subcutaneous injection), enteral, transmucosal (nasal, vaginal, rectal, or sublingual), or transdermal (either passively or using iontophoresis or electroporation) routes of administration or using bioerodible inserts and can be formulated in dosage forms appropriate for each route of administration.

In certain embodiments, the compositions are administered locally, for example by injection directly into a site to be treated (e.g., into a tumor). In some embodiments, the compositions are injected or otherwise administered directly into the vasculature onto vascular tissue at or adjacent to the intended site of treatment (e.g., adjacent to a tumor). Typically, local administration causes an increased localized concentration of the composition which is greater than that which can be achieved by systemic administration.

a. Formulations for Parenteral Administration

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Formulations may be prepared using a pharmaceutically acceptable carrier. As generally used herein "carrier" includes, but is not limited to, diluents, preservatives, binders, lubricants, disintegrators, swelling agents, fillers, stabilizers, and combinations thereof.

Carrier also includes all components of the coating composition, which may include plasticizers, pigments, colorants, stabilizing agents, and glidants. Delayed release dosage formulations may be prepared as described in standard references. These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions, which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Dosage Forms

The extended release formulations are generally prepared as diffusion or osmotic systems, which are known in the art. A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers. In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids. The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers may also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules, etc. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Dosage Forms

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

c. Formulations for Pulmonary and Mucosal Administration

Active agent(s) and compositions thereof can be applied formulated for pulmonary or mucosal administration. The administration can include delivery of the composition to the lungs, nasal, oral (sublingual, buccal), vaginal, or rectal mucosa.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different EGS may be administered to target different regions of the lung in one administration.

Formulations for pulmonary delivery include unilamellar phospholipid vesicles, liposomes, or lipoprotein particles. Formulations and methods of making such formulations containing nucleic acid are well known to one of ordinary skill in the art. Liposomes are formed from commercially available phospholipids supplied by a variety of vendors including Avanti Polar Lipids, Inc. (Birmingham, Ala.). In one embodiment, the liposome can include a ligand molecule specific for a receptor on the surface of the target cell to direct the liposome to the target cell.

d. Transdermal

Transdermal formulations may also be prepared. These will typically be ointments, lotions, sprays, or patches, all of which can be prepared using standard technology. Transdermal formulations can include penetration enhancers.

III. Methods of Selectively Inhibiting Akt3

The disclosed compositions for selectively inhibiting Akt3 can be used to modulate an immune response decreasing a suppressive function of nTregs. In some embodiments, Formula I is administered systemically. In other embodiments, Formula I is administered locally or regionally. For example, in some embodiments, compositions containing Formula I and optionally, one or more of compounds 1-28 are delivered to or specifically target the tissue or organs in need of modulation. Tregs can be modulated by targeting or delivering the compositions to the lymph nodes. nTregs can be modulated by targeting or specifically delivering the compositions to the thymus or spleen. iTregs can be modulated by targeting or specifically delivering the compositions to conventional T cells outside the thymus.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. Exemplary symptoms, pharmacologic, and physiologic effects are discussed in more detail below.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based measuring the symptom, pharmacologic, or physiologic indicator in one or more subjects that do not have the disease or condition to be treated (e.g., healthy subjects). In some embodiments, the effect of the treatment is compared to a conventional treatment that is known the art. For example, if the disease to be treated is cancer, and conventional treatment could a chemotherapeutic agent.

In some embodiments, the immune modulating compositions disclosed herein are administered in combination with one or more additional active agents. The combination therapies can include administration of the active agents together in the same admixture, or in separate admixtures. Therefore, in some embodiments, the pharmaceutical composition includes two, three, or more active agents. The pharmaceutical compositions can be formulated as a pharmaceutical dosage unit, referred to as a unit dosage form. Such formulations typically include an effective amount of one or more of the disclosed immune modulating compounds. The different active agents can have the same, or different mechanisms of action. In some embodiments, the combination results in an additive effect on the treatment of the disease or disorder. In some embodiments, the combinations result in a more than additive effect on the treatment of the disease or disorder.

Preferably, the disclosed compounds and methods of use specifically inhibit the activity of Akt3 without increasing or decreasing the activity of Akt1, Akt2, or the combination thereof.

A. Decreasing Immune Suppressive Responses and Increasing Immune Stimulatory Responses 1. Methods of Treatment In some embodiments compositions that decrease the bioactivity of Akt3 are administered to a subject in an effective amount to increase an immune stimulatory response, decrease an immune suppressive response, or a combination thereof. Akt3 regulates the function and induction of natural and induced Tregs. Therefore Akt3 expression levels can be modulated to alter the function and induction of Tregs. In some embodiments, a composition that selectively inhibits Akt3 is administered to a subject in an effective amount to decrease a suppressive function of nTreg, to decrease the induction of conventional Treg into iTreg, or a combination thereof. In some embodiments, a decrease in the suppressive function of nTreg is measured as an overall decrease in secretion or presence of pro-inflammatory cytokines or chemokines, for example, TGFβ and IL10. Other pro-inflammatory molecules that can be decreased include, but are not limited to, IL-1β, TNF-α, IFN-γ, IL-17, IL-6, IL-23, IL-22, IL-21, and MMPs. Induction of conventional Treg into iTreg can be measured as differentiation of CD4+CD25− cells into Foxp3+ cells. In some embodiments, this is measured as an increase in the number of CD4+ conventional T cells, or a decrease in the number of Foxp3+ T cells.

2. Diseases to Treat

Compositions containing Formula I and optionally, one or more of compounds 1-28 that selectively inhibit Akt3 can be used to increase an immune stimulatory response in subject. In some embodiments, the subjects have cancer, an infectious disease, or another condition in which the immune response is desired. In some embodiments, the subject does not have cancer or does not have an infectious disease. In some embodiments, the subject has an infectious disease, but does not have cancer. In some embodiments, the subject has cancer, but does not have an infectious disease.

a. Cancer

Formula I for selectively inhibiting Akt3 is generally useful in vivo and ex vivo as immune response-stimulating therapeutics. In general, Formula I is useful for treating a subject having or being predisposed to any disease or disorder to which the subject's immune system mounts an immune response. The ability of Formula I to inhibit Akt3 and thereby inhibit or reduce Treg mediated immune suppression enables a more robust immune response to be possible. Formula I is also useful to stimulate or enhance immune stimulating or activating responses involving T cells.

Formula I is useful for stimulating or enhancing an immune response in a host for treating cancer by selectively inhibiting Akt3. Formula I can be administered to a subject in an amount effective to stimulate T cells in the subject. The types of cancer that can be treated with Formula I include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors that can be treated can be classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

b. Infections

Formula I is generally useful in vivo and ex vivo as immune response-stimulating therapeutics. In a preferred embodiment, Formula I is useful for treating infections in which T cell exhaustion or T cell anergy has occurred causing the infection to remain with the host over a prolonged period of time. Exemplary infections to be treated are chronic infections cause by a hepatitis virus, a human immunodeficiency virus (HIV), a human T-lymphotrophic virus (HTLV), a herpes virus, an Epstein-Barr virus, or a human papilloma virus. It will be appreciated that other infections can also be treated using Formula I for decreasing the bioavailability of Akt3. Formula I is also useful as part of a vaccine. In a preferred embodiment, the type of disease to be treated or prevented is a chronic infectious disease caused by a bacterium, virus, protozoan, helminth, or other microbial pathogen that enters intracellularly and is attacked, i.e., by cytotoxic T lymphocytes.

Chronic infections in human and animal models are associated with a failure of the host immune response to generate and sustain functional CD8$^+$ and CD4$^+$ T-cell populations, which also results in poor antibody responses to neutralize infectivity. This loss of function is referred to as T cell exhaustion. T cell anergy is a tolerance mechanism in which the lymphocyte is intrinsically functionally inactivated following an antigen encounter, but remains alive for an extended period of time in a hyporesponsive state. One method for treating chronic infection is to revitalize exhausted T cells or to reverse T cell exhaustion in a subject as well as overcoming T cell anergy. Therefore, in some embodiments, Formula I is administered to a subject in an effective amount to reverse T cell exhaustion, overcoming T cell anergy, or a combination thereof in a subject in need thereof.

Because viral infections are cleared primarily by T-cells, an increase in T-cell activity is therapeutically useful in situations where more rapid or thorough clearance of an infective viral agent would be beneficial to an animal or human subject. Thus, Formula I can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including Formula I can be administered topically to treat viral skin diseases such as herpes lesions or shingles, or genital warts. Pharmaceutical formulations containing Formula I can also be administered to treat systemic viral diseases, including, but not limited to, AIDS, influenza, the common cold, or encephalitis.

Representative infections that can be treated, include but are not limited to infections cause by microoganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus influenza type B (HIB), *Histoplasma, Hyphomicrobium, Legionella, Leishmania, Leptspirosis, Listeria*, Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni*.

3. Use of Compounds for Selective Inhibition of Akt3 in Vaccines a. Vaccine-Related Methods Formula I selectively inhibits Akt3 can be administered alone or in combination with any other suitable treatment, including but not limited to compounds 1-28. In one embodiment Formula I can be administered in conjunction with, or as a component of a vaccine composition. The disclosed compounds can be administered prior to, concurrently with, or after the administration of a vaccine. In one embodiment the compound is administered at the same time as administration of a vaccine.

Formula I can be administered in conjunction with prophylactic vaccines, which confer resistance in a subject to subsequent exposure to infectious agents, or in conjunction with therapeutic vaccines, which can be used to initiate or enhance a subject's immune response to a pre-existing antigen, such as a viral antigen in a subject infected with a virus.

The desired outcome of a prophylactic, therapeutic or de-sensitized immune response may vary according to the disease, according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

Formula I can induce an improved effector cell response such as a CD4 T-cell immune response, against at least one of the component antigen(s) or antigenic compositions compared to the effector cell response obtained with the corresponding composition without the compound. The term "improved effector cell response" refers to a higher effector cell response such as a CD4 T cell response obtained in a human patient after administration of the vaccine composition than that obtained after administration of the same composition without a compound for decreasing the bioavailability of Akt3. Such a formulation can advantageously be used to induce anti-antigen effector cell response capable of detection of antigen epitopes presented by MHC class II molecules.

The improved effector cell response can be obtained in an immunologically unprimed patient, i.e. a patient who is seronegative to the antigen. This seronegativity may be the result of the patient having never faced the antigen (so-called "naïve" patient) or, alternatively, having failed to respond to the antigen once encountered. Preferably the improved effector cell response is obtained in an immunocompromised subject such as an elderly, typically 65 years of age or above, or an adult younger than 65 years of age with a high risk medical condition ("high risk" adult), or a child under the age of two.

The improved effector cell response can be assessed by measuring the number of cells producing any of the following cytokines: (1) cells producing at least two different cytokines (CD40L, IL-2, IFNγ, TNF-α, IL-17); (2) cells producing at least CD40L and another cytokine (IL-2, TNF-α, IFNγ, IL-17); (3) cells producing at least IL-2 and another cytokine (CD40L, TNF-alpha, IFNγ, IL-17); (4) cells producing at least IFNγ and another cytokine (IL-2, TNF-α, CD40L, IL-17); (5) cells producing at least TNF-α and another cytokine (IL-2, CD40L, IFNγ, IL-17); and (6) cells producing at least IL-17 and another cytokine (TNF-alpha, IL-2, CD40L, IFNγ, IL-17)

An improved effector cell response is present when cells producing any of the above cytokines will be in a higher amount following administration of the vaccine composition compared to the administration of the composition without a compound for decreasing the bioavailability of Akt3. Typically at least one, preferably two of the five conditions mentioned above will be fulfilled. In a preferred embodiment, cells producing all five cytokines (CD40L, IL-2, IFNγ, TNF-α, IL-17) will be present at a higher number in the vaccinated group compared to the un-vaccinated group.

The immunogenic compositions may be administered by any suitable delivery route, such as intradermal, mucosal e.g. intranasal, oral, intramuscular or subcutaneous. Other delivery routes are well known in the art. The intramuscular delivery route is preferred for the immunogenic compositions. Intradermal delivery is another suitable route. Any suitable device may be used for intradermal delivery, for example short needle devices. Intradermal vaccines may also be administered by devices which limit the effective penetration length of a needle into the skin. Jet injection devices which deliver liquid vaccines to the dermis via a liquid jet injector or via a needle which pierces the stratum corneum and produces a jet which reaches the dermis can also be used. Jet injection devices are known in the art. Ballistic powder/particle delivery devices which use compressed gas to accelerate vaccine in powder form through the outer layers of the skin to the dermis can also be used. Additionally, conventional syringes can be used in the classical Mantoux method of intradermal administration.

Another suitable administration route is the subcutaneous route. Any suitable device may be used for subcutaneous delivery, for example classical needle. Preferably, a needle-free jet injector service is used. Needle-free injectors are known in the art. More preferably the device is pre-filled with the liquid vaccine formulation.

Alternatively the vaccine is administered intranasally. Typically, the vaccine is administered locally to the nasopharyngeal area, preferably without being inhaled into the lungs. It is desirable to use an intranasal delivery device which delivers the vaccine formulation to the nasopharyngeal area, without or substantially without it entering the lungs. Preferred devices for intranasal administration of the vaccines are spray devices. Nasal spray devices are commercially available. Nebulizers produce a very fine spray which can be easily inhaled into the lungs and therefore does not efficiently reach the nasal mucosa. Nebulizers are therefore not preferred. Preferred spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are commercially available.

Preferred intranasal devices produce droplets (measured using water as the liquid) in the range 1 to 200 preferably 10 to 120 Below 10 μm there is a risk of inhalation, therefore it is desirable to have no more than about 5% of droplets below 10 Droplets above 120 μm do not spread as well as smaller droplets, so it is desirable to have no more than about 5% of droplets exceeding 120

Bi-dose delivery is another feature of an intranasal delivery system for use with the vaccines. Bi-dose devices contain two sub-doses of a single vaccine dose, one sub-dose for administration to each nostril. Generally, the two sub-doses are present in a single chamber and the construction of the device allows the efficient delivery of a single sub-dose at a time. Alternatively, a monodose device may be used for administering the vaccines.

The immunogenic composition may be given in two or more doses, over a time period of a few days, weeks or months. In one embodiment, different routes of administration are utilized, for example, for the first administration may be given intramuscularly, and the boosting composition can be administered through a different route, for example intradermal, subcutaneous or intranasal.

The improved effector cell response conferred by the immunogenic composition may be ideally obtained after one single administration. The single dose approach is extremely relevant in a rapidly evolving outbreak situation including bioterrorist attacks and epidemics. In certain circumstances, especially for the elderly population, or in the case of young children (below 9 years of age) who are vaccinated for the first time against a particular antigen, it may be beneficial to administer two doses of the same composition. The second dose of the same composition (still considered as 'composition for first vaccination') can be administered during the on-going primary immune response and is adequately spaced in time from the first dose. Typically the second dose of the composition is given a few weeks, or about one month, e.g. 2 weeks, 3 weeks, 4 weeks, 5 weeks, or 6 weeks after the first dose, to help prime the immune system in unresponsive or poorly responsive individuals.

In a specific embodiment, the administration of the immunogenic composition alternatively or additionally induces an improved B-memory cell response in patients administered with the adjuvanted immunogenic composition compared to the B-memory cell response induced in individuals immunized with the un-adjuvanted composition. An improved B-memory cell response is intended to mean an increased frequency of peripheral blood B lymphocytes capable of differentiation into antibody-secreting plasma cells upon antigen encounter as measured by stimulation of in vitro differentiation (see Example sections, e.g. methods of Elispot B cells memory).

In a still another embodiment, the immunogenic composition increases the primary immune response as well as the CD8 T cell response. The administration of a single dose of the immunogenic composition for first vaccination provides better sero-protection and induces an improved CD4 T-cell, or CD8 T-cell immune response against a specific antigen compared to that obtained with the un-adjuvanted formulation. This may result in reducing the overall morbidity and mortality rate and preventing emergency admissions to hospital for pneumonia and other influenza-like illness. This method allows inducing a CD4 T cell response which is more persistent in time, e.g. still present one year after the first vaccination, compared to the response induced with the un-adjuvanted formulation.

Preferably the CD4 T-cell immune response, such as the improved CD4 T-cell immune response obtained in an unprimed subject, involves the induction of a cross-reactive CD4 T helper response. In particular, the amount of cross-reactive CD4 T cells is increased. The term "cross-reactive" CD4 response refers to CD4 T-cell targeting shared epitopes for example between influenza strains.

b. Immunogenic and Vaccine Compositions Formula I can enhance an immune response to an antigen in a human. As discussed above, Formula I can be administered as a component of a vaccine to promote, augment, or enhance the primary immune response and effector cell activity and numbers. When used as part of a vaccine, Formula I can be administered in separate, or in the same admixture with an immunogenic composition or as part of an immunogenic protocol. Vaccines include antigens, and optionally other adjuvants and targeting molecules.

i. Antigens

Antigens can be peptides, proteins, polysaccharides, saccharides, lipids, nucleic acids, or combinations thereof. The antigen can be derived from a virus, bacterium, parasite, protozoan, fungus, histoplasma, tissue or transformed cell and can be a whole cell or immunogenic component thereof, e.g., cell wall components or molecular components thereof.

Suitable antigens are known in the art and are available from commercial, government and scientific sources. In one embodiment, the antigens are whole inactivated or attenuated organisms. These organisms may be infectious organisms, such as viruses, parasites and bacteria. The antigens may be tumor cells or cells infected with a virus or intracellular pathogen such as gonorrhea or malaria. The antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids.

(a) Viral Antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain, or a combination of strains, such as a papilloma virus, a herpes virus, i.e. herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

(b) Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus influenza type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

(c) Parasitic Antigens

Antigens of parasites can be obtained from parasites such as, but not limited to, antigens derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

(d) Tumor Antigens

The antigen can be a tumor antigen, including a tumor-associated or tumor-specific antigen, such as, but not limited to, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-1, 2, and 3, neo-PAP, myosin class I, OS-9, pml-RARα fusion protein, PTPRK, K-ras, N-ras, Triosephosphate isomeras, Bage-1, Gage 3,4,5,6,7, GnTV, Herv-K-mel, Lage-1, Mage-A1,2,3,4,6,10,12, Mage-C2, NA-88, NY-Eso-1/Lage-2, SP17, SSX-2, and TRP2-Int2, MelanA (MART-I), gp100 (Pmel 17), tyrosinase, TRP-1, TRP-2, MAGE-1, MAGE-3, BAGE, GAGE-1, GAGE-2, p15(58), CEA, RAGE, NY-ESO (LAGE), SCP-1, Horn/Mel-40, PRAME, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, β-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90 (Mac-2 binding protein\cyclophilin C-associated protein), TAAL6, TAG72, TLP, and TPS. Tumor antigens, such as BCG, may also be used as an immunostimulant to adjuvant.

ii. Adjuvants

Optionally, the vaccines may include an adjuvant. The adjuvant can be, but is not limited to, one or more of the following: oil emulsions (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants may also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor. Other co-stimulatory molecules, including other polypeptides of the B7 family, may also be administered. Such proteinaceous adjuvants may be provided as the full-length polypeptide or an active fragment thereof, or in the form of DNA, such as plasmid DNA.

4. Combination Therapies

Formula I can be administered alone or in combination with one, two, three, or more additional active agents. In some embodiments, the additional active agent is one that is known in the art for treatment of cancer, infections, or administered in combination with a vaccine, etc. The additional therapeutic agents are selected based on the condition, disorder or disease to be treated. For example, compositions for selectively inhibiting Akt3 can be co-administered with one or more additional agents that function to enhance or promote an immune response.

For example, Formula I can be administered with an antibody or antigen binding fragment thereof specific for a growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cekl); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Axl; RYK; DDR; and Tie.

Additional therapeutic agents include conventional cancer therapeutics such as chemotherapeutic agents, cytokines, chemokines, and radiation therapy. The majority of chemotherapeutic drugs can be divided in to: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and tyrosine kinase inhibitors e.g. imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to cisplatin, carboplatin, doxorubicin, oxaliplatin, mechlorethamine, cyclophosphamide, chlorambucil, vincristine, vinblastine, vinorelbine, vindesine, taxol and derivatives thereof, irinotecan, topotecan, amsacrine, etoposide, etoposide phosphate, teniposide, epipodophyllotoxins, trastuzumab (HERCEPTIN®), cetuximab, and rituximab (RITUXAN® or MABTHERA®), bevacizumab (AVASTIN®), and combinations thereof.

In a preferred embodiment, the additional therapeutic agent is cyclophosphamide. Cyclophosphamide (CPA, Cytoxan, or Neosar) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANAO) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Ref. Liang J, Huang M, Duan W, Yu X Q, Zhou S. Design of new oxazaphosphorine anticancer drugs. Curr Pharm Des. 2007; 13(9):963-78. Review). These include mafosfamide (NSC 345842), glufosfamide (D19575, beta-D-glucosylisophosphoramide mustard), S-(-)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

Additional therapeutic agents include is an agent that reduces activity and/or number of regulatory T lymphocytes (T-regs), preferably Sunitinib (SUTENT®), or anti-TGFβ. Other additional therapeutic agents include mitosis inhibitors, such as paclitaxel, aromatase inhibitors (e.g. Letrozole), angiogenesis inhibitors (VEGF inhibitors e.g. Avastin, VEGF-Trap), TLR4 antagonists, and IL-18 antagonists.

V. Kits

Medical kits are also disclosed. The medical kits can include, for example, a dosage supply of Formula I. Formula I can be supplied alone (e.g., lyophilized), or in a pharmaceutical composition. Formula I can be in a unit dosage, or in a stock that should be diluted prior to administration. In some embodiments, the kit includes a supply of pharmaceutically acceptable carrier. The kit can also include devices for administration of the active agent(s) or composition(s), for example, syringes. The kits can include printed instructions for administering Formula I in a use as described above.

EXAMPLES

Example 1: 4-[(6-nitroquinolin-4-yl)amino]-N-[4-(pyridin-4-ylamino)phenyl]benzamide (Formula 1) Inhibits Akt3 but not Akt1 Phosphorylation in Tregs Materials and Methods FACS-sorted natural regulatory T cells (nTregs), from WT C57BL/6J (foxp3-GFP) mice were plated on anti-CD3-coated plates and cultured in activation media (IL2 and anti-CD28) without inhibitors (Stimulated) and with different concentrations of inhibitor 4-[(6-nitroquinolin-4-yl)amino]-N-[4-(pyridin-4-ylamino)phenyl]benzamide (also referred to as JJ64-E) for 72 hrs. For negative control (Non-stimulated-NS) cells were left in media containing IL-2 for 72 hrs. nTreg cell lysates prepared on day 3 (72 hrs) of treatment were separated by SDS-PAGE and immunoblotted with specific antibodies (pAkt1) or pAkt3; actin was used as loading control.

Results

The data show 4-[(6-nitroquinolin-4-yl)amino]-N-[4-(pyridin-4-ylamino)phenyl]benzamide inhibits Akt3 but not Akt1 phosphorylation in Tregs.

Example 2: 4-[(6-nitroquinolin-4-yl)amino]-N-[4-(pyridin-4-ylamino)phenyl]benzamide (Formula 1) Selectively Inhibits Treg Proliferation Materials and Methods FACS-sorted nTregs, CD4+ and CD8+ T cells from C57BL/6J(foxp3-GFP) were plated on anti-CD3-coated plates and cultured in activation media (IL2 and anti-CD28) without inhibitors (Stimulated) and with inhibitors (JJ64-E) for 72 hrs. For negative control (Non-stimulated-NS) cells were left in media containing IL-2 for 72 hrs. After 72 hrs Proliferation (level of VCT) in live gated cells was measured by flow cytometry.

Results

The data show that 4-[(6-nitroquinolin-4-yl)amino]-N-[4-(pyridin-4-ylamino)phenyl]benzamide selectively inhibits Treg proliferation sparing CD8 and other CD4 T cells.

Example 3: 4-[(6-nitroquinolin-4-yl)amino]-N-[4-(pyridin-4-ylamino)phenyl]benzamide Decreases Tegs In Vivo in TC-1 Tumor Model Materials and Methods WT C57BL/6J mice (n=3/group) were injected s.c. in the right flank with $7 \times 10^4$ TC-1 cells. Mice from appropriate groups were treated with either 5 mg/kg or 10 mg/kg of JJ64-E injected (i.p.) every day starting on day 10 after tumor implantation throughout the experiment. All groups were euthanized on day 15 of TC-1 implantation. The percentage of Tregs (CD4+Foxp3+) was analyzed by flow cytometry.

Statistical significance was determined by one-way ANOVA with Tukey's multiple comparison test (*, p<0.05; , p<0.01; *, p<0.001).

Results

4-[(6-nitroquinolin-4-yl)amino]-N-[4-(pyridin-4-ylamino)phenyl]benzamide decreases Tegs in vivo in TC-1 tumor model

Example 4: 4-[(6-nitroquinolin-4-yl)amino]-N-[4-(pyridin-4-ylamino)phenyl]benzamide (Formula 1 or JJ64-E) does not Affect CD8 and Other (FoxP3neg) CD4 T Cells in TC-1 Tumor Model Materials and Methods WT C57BL/6 4-6 weeks old female mice (n=5/group) were injected s.c. in the right flank with 7×104 TC-1 cells. Mice from appropriate groups were treated with either 5 mg/kg or 10 mg/kg of JJ64-E injected (i.p.) everyday starting on day 10 after tumor implantation throughout the experiment. All groups were euthanized on day 15 of TC-1 implantation. The percentage of CD4 and CD8 were analyzed in splenic CD4+ cells by flow cytometry.

Results

4-[(6-nitroquinolin-4-yl)amino]-N-[4-(pyridin-4-ylamino)phenyl]benzamide does not affect CD8 and other (FoxP3neg) CD4 T cells in TC-1 tumor model.

Example 5: 4-[(6-nitroquinolin-4-yl)amino]-N-[4-(pyridin-4-ylamino)phenyl]benzamide (in Both Applications Formula 1 or JJ64-E) Inhibits TC-1 Tumor Growth and Prolongs the Survival at High Dose as Monotherapy and at Lower Dose when Combined with Vaccine Materials and Methods C57BL/6 mice (n=5/group) were injected s.c. in the right flank with $7 \times 10^4$ TC-1 cells. Mice from appropriate groups were injected weekly with vaccine (s.c.) or DMSO 5% as a control. Mice were also treated with vaccine (weekly) along with either 10 mg/kg or 20 mg/kg of JJ64-E injected (i.p.) every day starting on day 6 after tumor implantation throughout the experiment.

FIGS. 5B and 5C are bar diagrams showing average tumor volumes of mice for each group. FIG. 5D is a Kaplan-Meier plot of the overall survival. Statistical significance was determined by Log-rank (Mantel-Cox) test.

Statistical significance was determined by one-way ANOVA with Tukey's multiple comparison test (*, p<0.05; , p<0.01; *, p<0.001).

Results

4-[(6-nitroquinolin-4-yl)amino]-N-[4-(pyridin-4-ylamino)phenyl]benzamide inhibits TC-1 tumor growth and prolongs the survival at high dose as monotherapy and at lower dose when combined with vaccine.

Example 6: JJ64-B Modification (Formula 3) Inhibits iTreg Induction

Materials and Methods

Figure 6A:
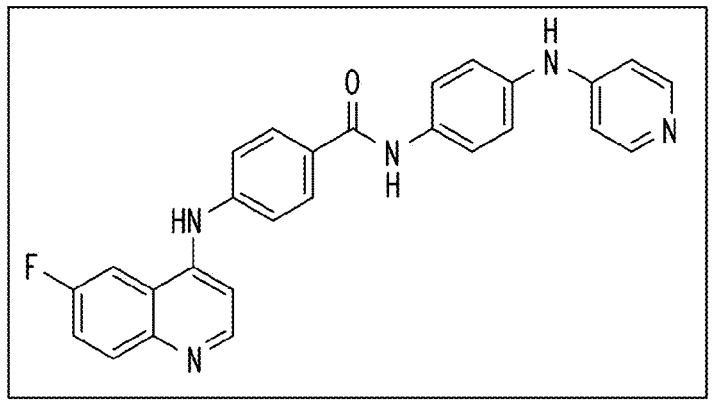
FIG. 6A is a structural diagram of compound (3) or JJ64-B.
Figures 6B, 6C, 6D:
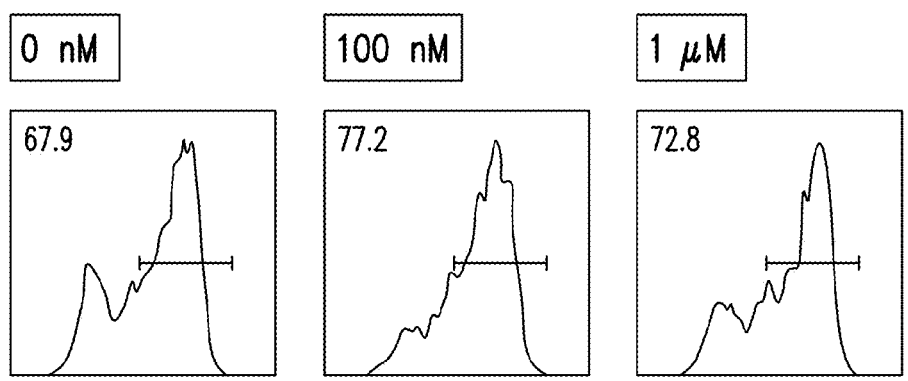
FIGS. 6B-6G are histograms of the frequency of CD4+FoxP3+ cells treated with compound (3) and measured by flow cytometry.
Figures 6E, 6F, 6G:
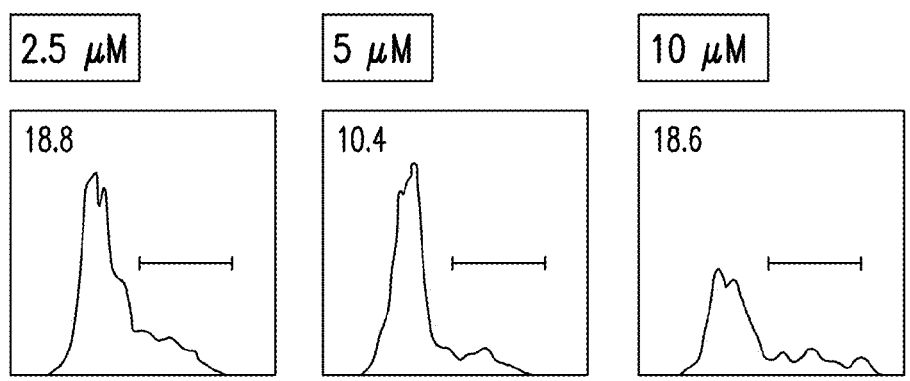
Figure 6H:
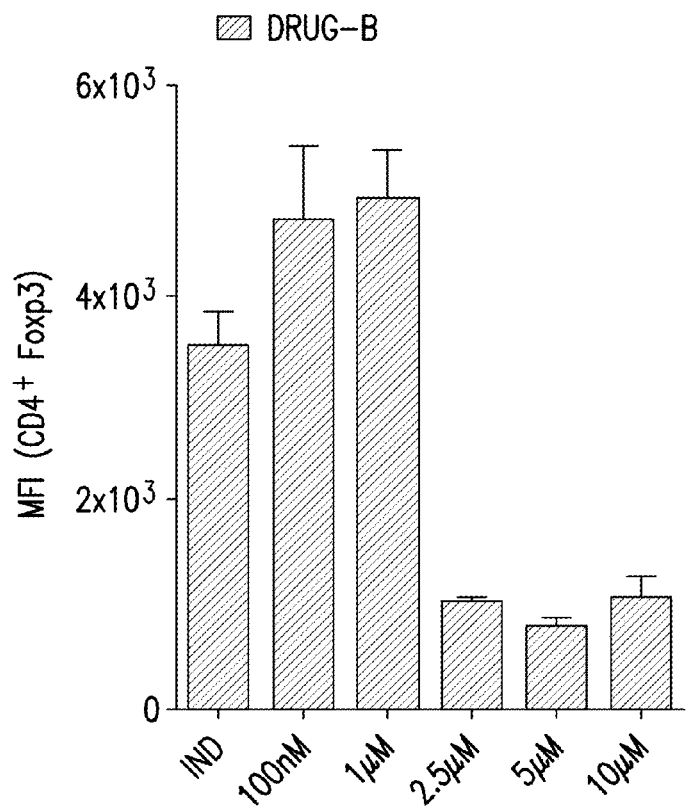
FIG. 6H is a bar graph of MFI (CD4+ Foxp3) of cells treated with compound (3).

FACS-sorted CD4+FoxP3− cells were plated on anti-CD3-coated plates with soluble IL2 and ant-CD28 with TGF-β (induction) Cell were induced for iTregs with JJ64-B (FIG. 6A) without inhibitor (Induction-IND)) or for 72 hrs. Cells were harvested and the frequency of CD4+FoxP3+ cells was measured by flow cytometry.

Results

JJ64-B (FIG. 6A) inhibits iTreg induction.

Figure 7A:
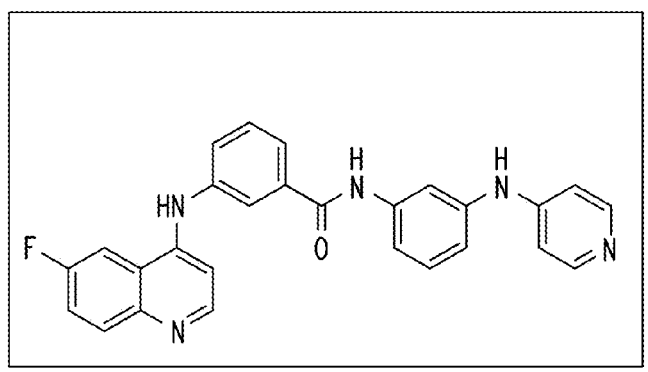
FIG. 7A is a structural diagram of compound (18).
Figure 7B:
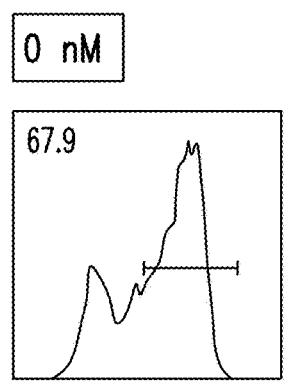
FIGS. 7B-7G are histograms of the frequency of CD4+FoxP3+ cells from animals treated with compound (18) and measured by flow cytometry.

Example 7: JJ64-C (FIG. 7A or Formula 18) Inhibits iTreg Induction

Materials and Methods

FACS-sorted CD4+FoxP3− cells were plated on anti-CD3-coated plates with soluble IL2 and ant-CD28 with TGF-β (induction) Cell were induced for iTregs with JJ64-C (JJ64 modified drug C or Formula 18) or without inhibitor (Induction-IND)) or for 72 hrs. Cells were harvested and the frequency of CD4+FoxP3+ cells was measured by flow cytometry.

Results

The data show that compound 18 (FIG. 7A) inhibits iTregs induction.

Example 8: JJ64-C (FIG. 7A or Formula 18) Inhibits TC-1 Tumor Growth and Prolongs the Survival at High Dose as Monotherapy and at Lower Dose when Combined with Vaccine Materials and Methods C57BL/6 mice (n=5/group) were injected s.c. in the right flank with $7 \times 10^4$ TC-1 cells. Mice from appropriate groups were injected weekly with vaccine (s.c.) or DMSO 5% as a control. Mice were also treated with vaccine (weekly) along with either 10 mg/kg or 20 mg/kg of JJ64-C (or FIG. 7A or Formula 18) injected (i.p.) every other day starting on day 6 after tumor implantation throughout the experiment.

Figure 7C:
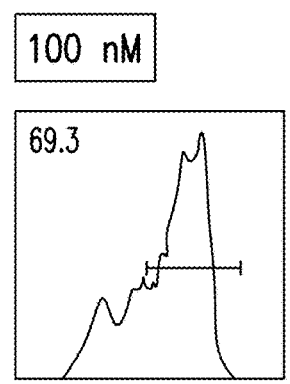
Figure 7D:
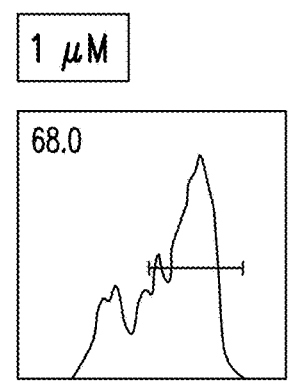
Figure 7E:
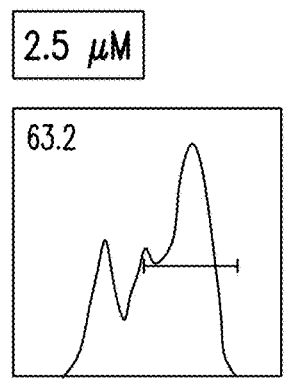
Figure 7F:
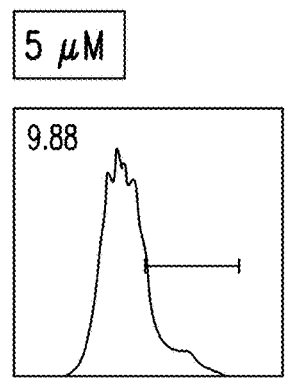
Figure 7G:
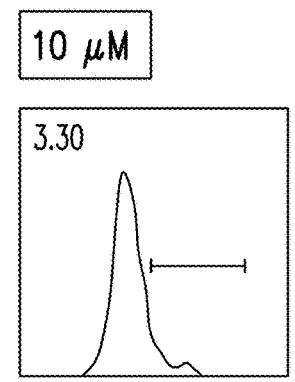
Figure 7H:
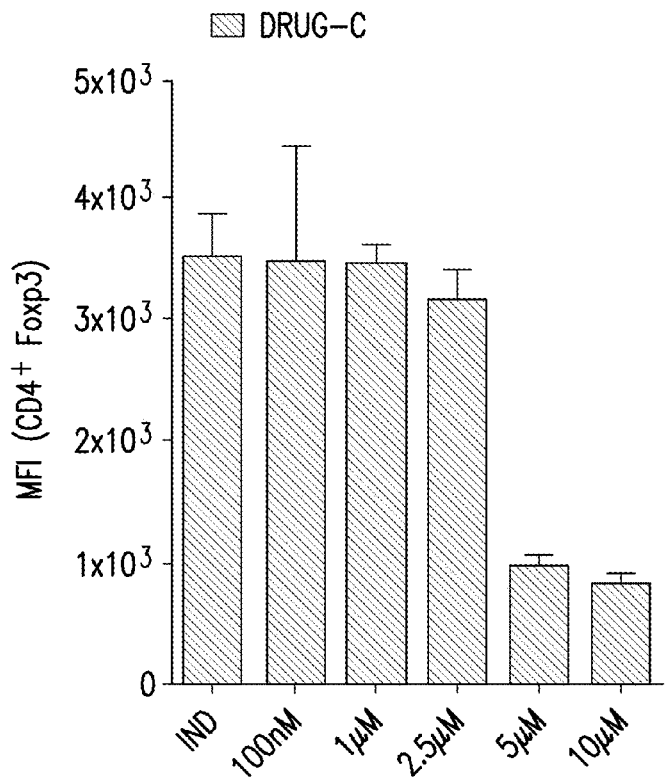
FIG. 7H is a bar graph of MFI (CD4+Foxp3) of cells treated with compound (18).
Figure 8A:
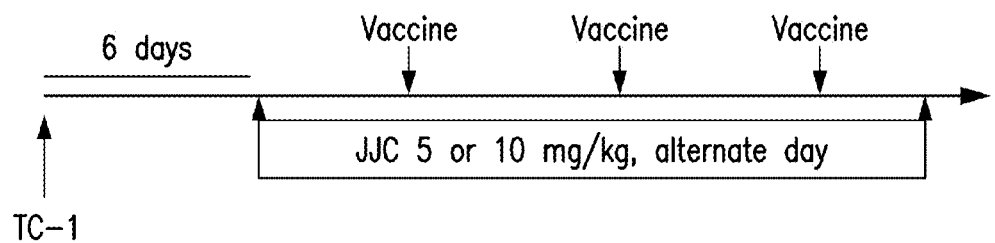
FIG. 8A is a schematic diagram of a treatment regimen.
Figure 8B:
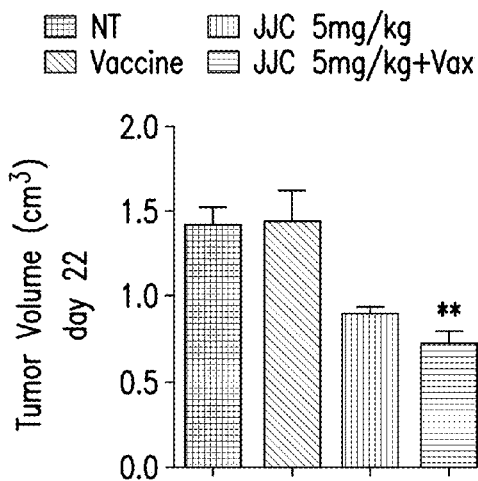
FIG. 8B is a bar graph of Tumor Volume ($cm^3$) of animals, from left to right, untreated, vaccine, 5 mg/kg compound (18), 5 mg/kg compound (18) and vaccine.
Figure 8C:
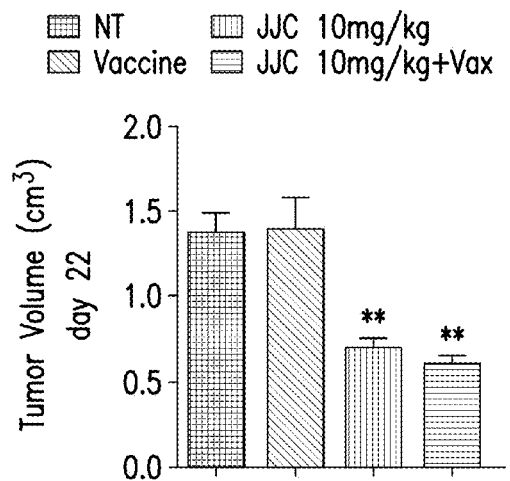
FIG. 8C is a bar graph of Tumor Volume ($cm^3$) of animals, from left to right, untreated, vaccine, 10 mg/kg compound (18), 10 mg/kg compound (18) and vaccine.
Figure 8D:
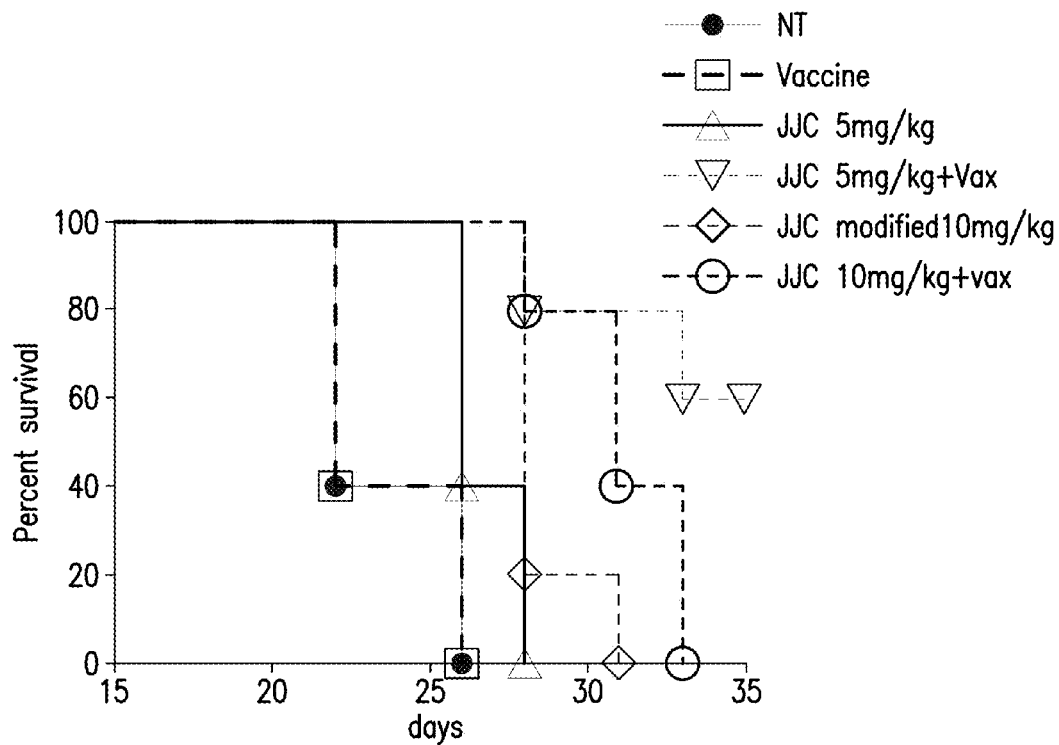
FIG. 8D is a Kaplan-Meier plot of the overall survival.

FIGS. 7C and 7D are bar diagrams representing average tumor volumes of mice for each group. FIG. 7E is a Kaplan-Meier plot of the overall survival. Statistical significance was determined by Log-rank (Mantel-Cox) test.

Statistical significance was determined by one-way ANOVA with Tukey's multiple comparison test (*, $p<0.05$; , $p<0.01$; *, $p<0.001$).

Results

JJ64-C (FIG. 7A or Formula 18) inhibits TC-1 tumor growth and prolongs the survival at high dose as monotherapy and at lower dose when combined with vaccine.

Figure 9A:
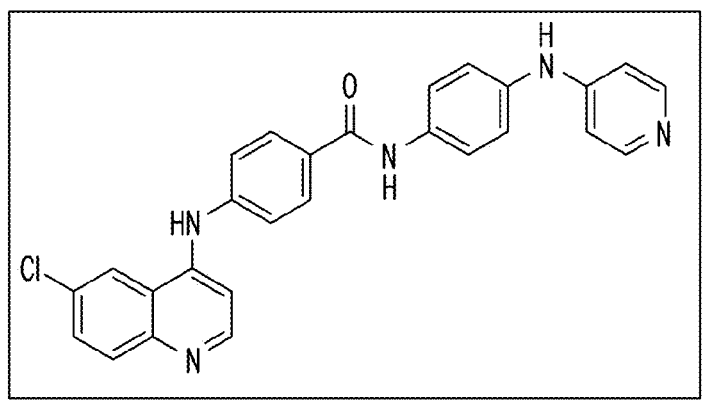
FIG. 9A is a structural diagram of a compound JJ64-D.
Figures 9B, 9C, 9D:
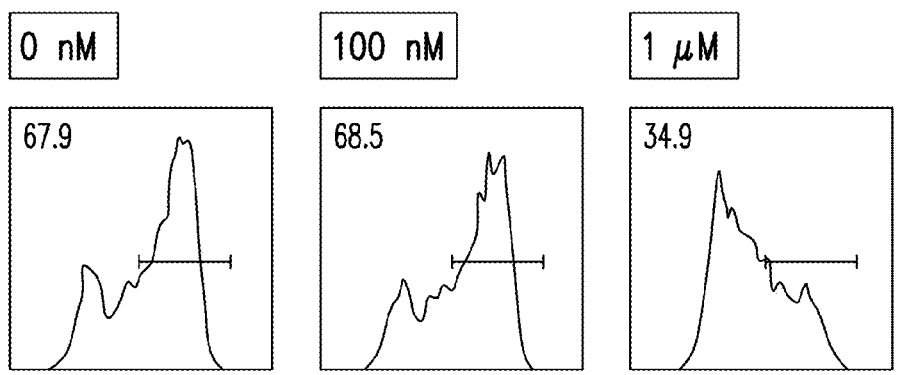
FIGS. 9B-9G are histograms of the frequency of CD4+ FoxP3+ cells from animals treated with JJ64-D and measured by flow cytometry.
Figures 9E, 9F, 9G:
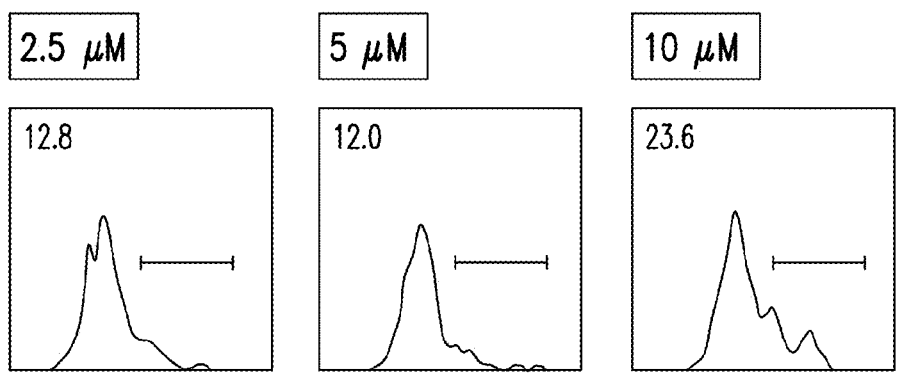
Figure 9H:
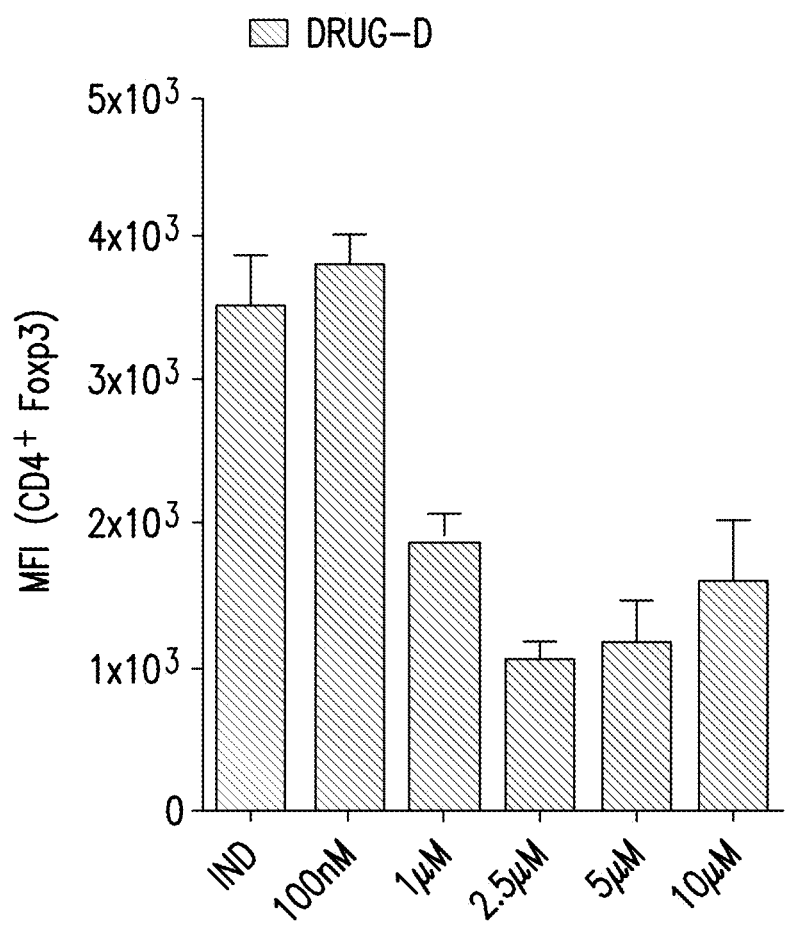
FIG. 9H is a bar graph of MFI (CD4+Foxp3) of cells treated with JJ64-D.

Example 9: JJ64-D (FIG. 9A) Inhibits iTreg Induction

Materials and Methods

FACS-sorted CD4+FoxP3− cells were plated on anti-CD3-coated plates with soluble IL2 and ant-CD28 with TGF-β (induction) Cell were induced for iTregs with JJ64-D (JJ64 modified drug D or FIG. 9A) or without inhibitor (Induction-IND)) or for 72 hrs. Cells were harvested and the frequency of CD4+FoxP3+ cells was measured by flow cytometry.

Results

JJ64-D (FIG. 9A) inhibits iTreg induction.

We claim:

1. A method of decreasing an immune suppressive response in a subject in need thereof comprising administering to the subject a composition comprising 0.01 to 50 mg/kg of 4-[(6-nitroquinolin-4-yl)amino]-N-[4-(pyridin-4-ylamino)phenyl]benzamide that selectively inhibits Akt3 by an amount effective to reduce the immune suppressive function of Tregs in the subject.

2. The method of claim 1 wherein the subject has cancer or an infection.

3. The method of claim 2, wherein the cancer is selected from the group consisting of bladder, brain, breast, cervical, colo-rectal, esophageal, kidney, liver, lung, nasopharangeal, pancreatic, prostate, skin, stomach, uterine, ovarian, testicular and hematologic cancers.

4. The method of claim 2, wherein the infectious disease is caused by bacterium, virus, protozoan, helminth, or other microbial pathogen.

5. The method of claim 1, wherein the immune suppressive response that is reduced is selected from the group consisting of an immune suppressive function of natural Treg (nTreg) and induction of conventional T cells into induced Treg (iTreg).

6. The method of claim 5 wherein the immune suppressive function of nTreg is the secretion of one or more anti-inflammatory cytokines.

7. The method of claim 6 wherein the anti-inflammatory cytokine is IL10, TGFβ, or a combination thereof.

8. The method of claim 1, further comprising administering to the subject a second active agent that is selected from the group consisting of chemotherapeutic agents, cytokines, chemokines, and radiation therapy.

9. The method of claim 1, further comprising administering to the subject a second Akt3 inhibitor that is a compound selected from the group consisting of (3)
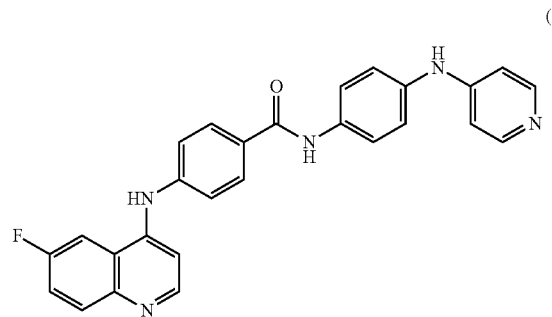
(4)
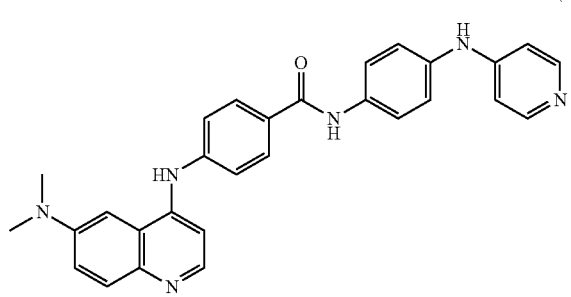
(5)
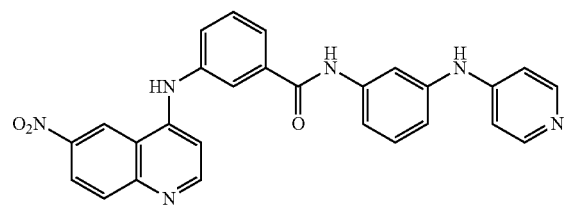
(6)
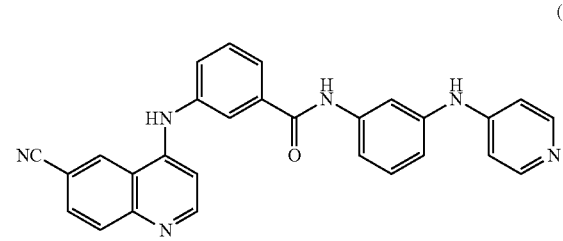
(7)
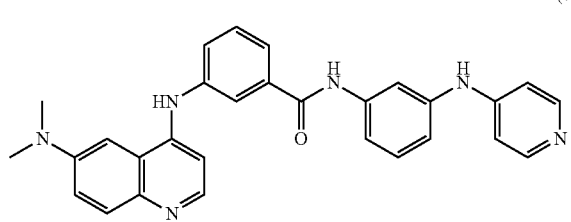
(8)
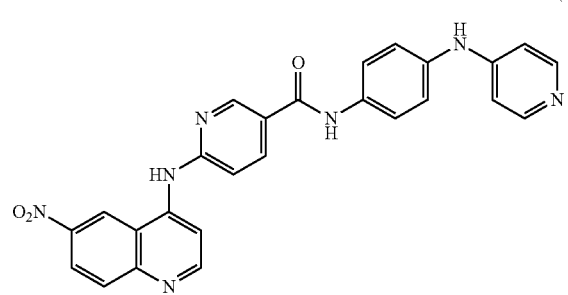
-continued
(9)
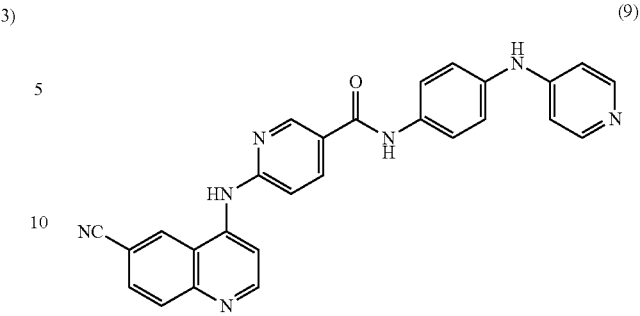
(10)
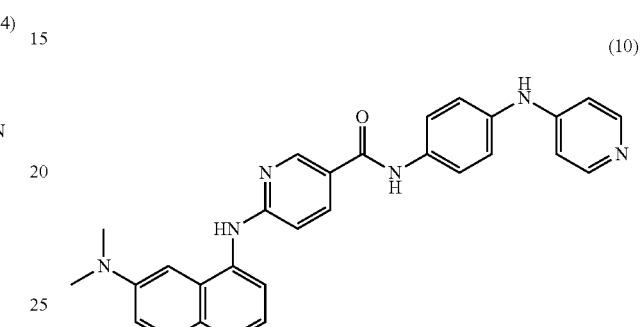
(11)
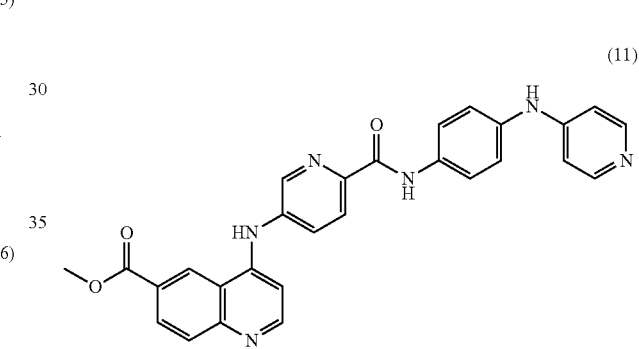
(12)
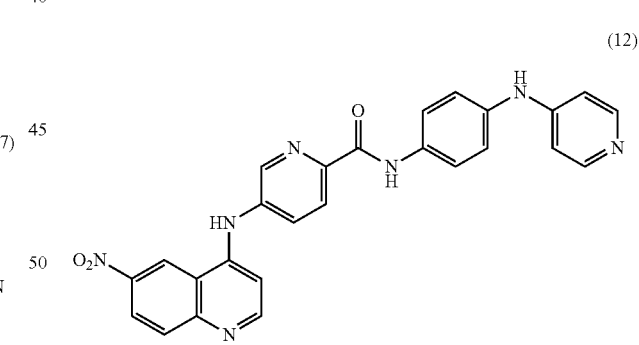
(13)
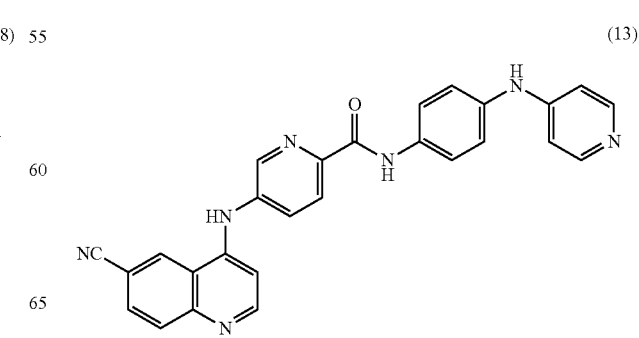

(14)
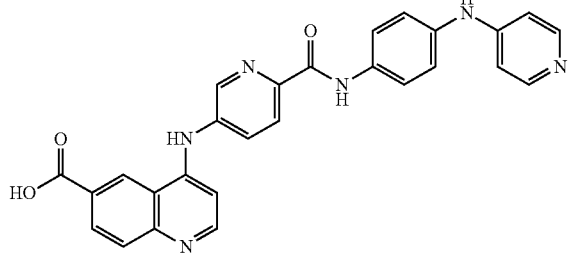
(15)
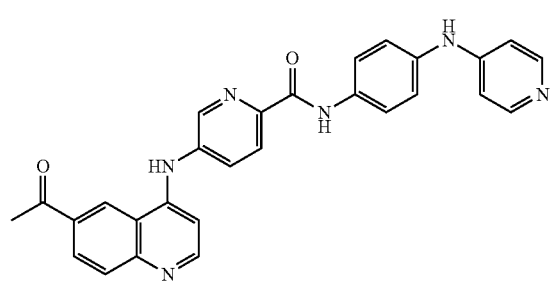
(16)
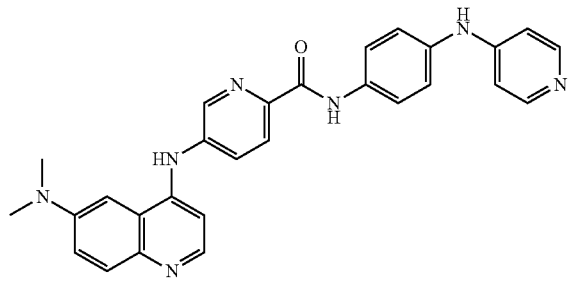
(17)
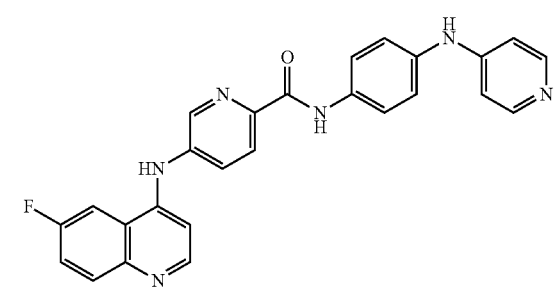
(18)
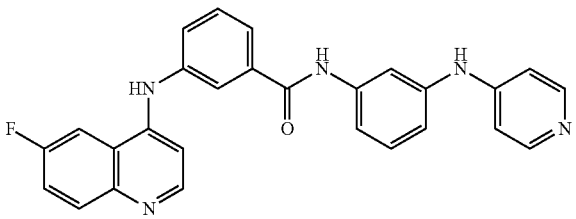
(19)
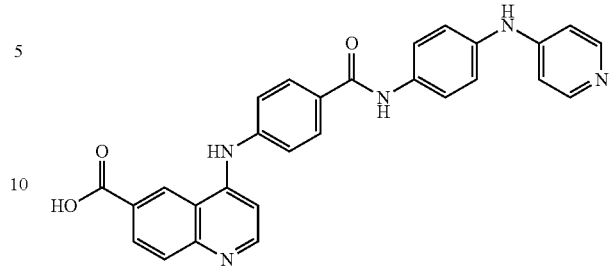
(20)
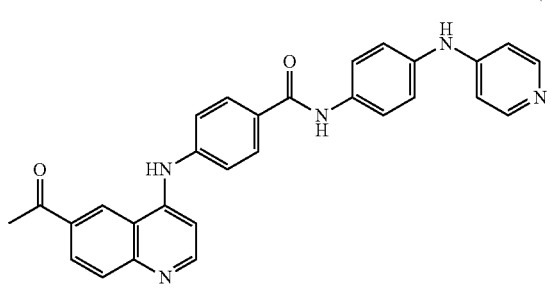
(21)
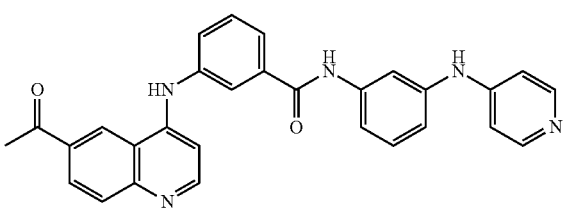
(22)
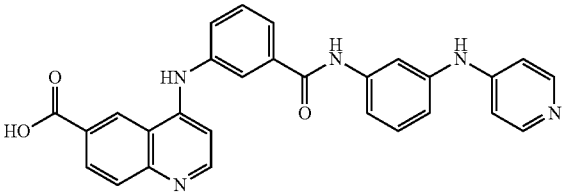
(23)
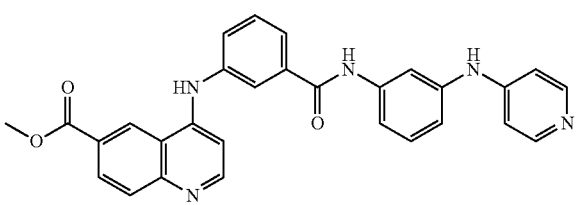
(24)
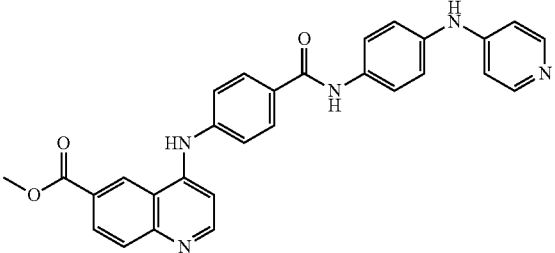

(25)
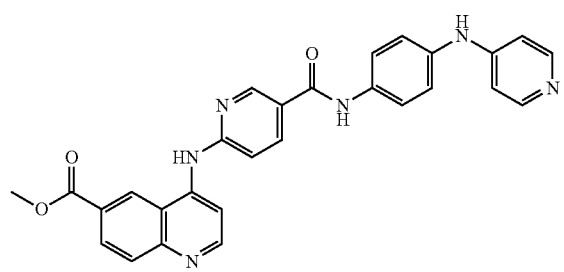
(26)
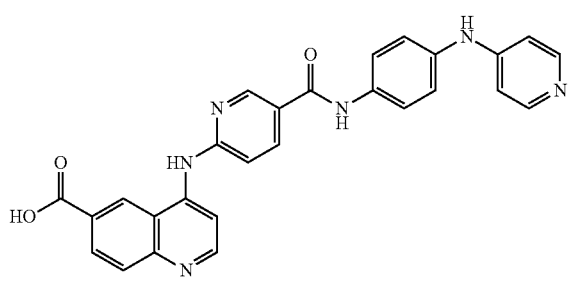
(27)
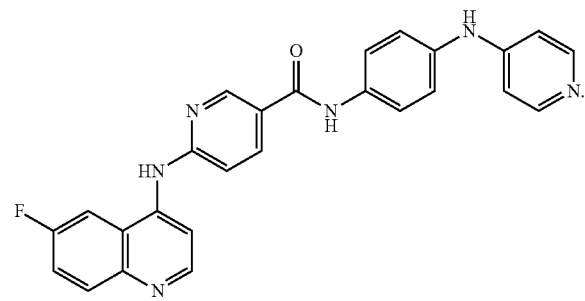
and
(28)
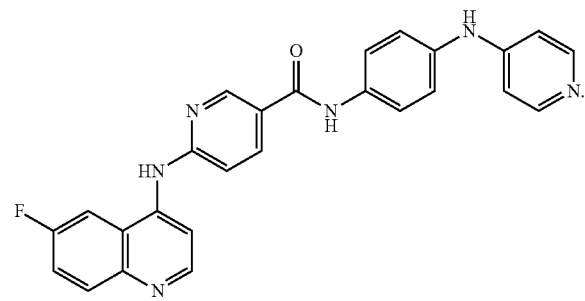
* * * * *

UNITED STATES PATENT AND TRADEMARK OFFICE
CERTIFICATE OF CORRECTION

PATENT NO. : 10,292,978 B2
APPLICATION NO. : 15/407659
DATED : May 21, 2019
INVENTOR(S) : Samir N. Khleif, Mikayel Mkrtichyan and Iryna Lebedyeva Page 1 of 1

It is certified that error appears in the above-identified patent and that said Letters Patent is hereby corrected as shown below:

On the Title Page

Column 1, Item (72) Remove inventor Iryna Lebedyeva.

Signed and Sealed this
Fourth Day of August, 2020

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 1708
<212> TYPE: DNA
<213> ORGANISM: homo sapiens

<400> SEQUENCE: 1 agggagtca tcatgagcga tgttaccatt gtgaaggaag gttgggttca gaagagggga      60
gaatatataa aaaactggag gccaagatac ttccttttga agacagatgg ctcattcata    120
ggatataaag agaaacctca agatgtggat ttaccttatc ccctcaacaa cttttcagtg    180
gcaaaatgcc agttaatgaa aacagaacga ccaaagccaa acacatttat aatcagatgt    240
ctccagtgga ctactgttat agagagaaca tttcatgtag atactccaga ggaaagggaa    300
gaatggacag aagctatcca ggctgtagca gacagactgc agaggcaaga agaggagaga    360
atgaattgta gtccaacttc acaaattgat aatataggag aggaagagat ggatgcctct    420
acaacccatc ataaaagaaa gacaatgaat gattttgact atttgaaact actaggtaaa    480 ggcactttg ggaaagttat tttggttcga gagaaggcaa gtgaaaata ctatgctatg    540 aagattctga agaaagaagt cattattgca aaggatgaag tggcacacac tctaactgaa    600
agcagagtat taaagaacac tagacatccc tttttaacat ccttgaaata ttccttccag    660
acaaaagacc gtttgtgttt tgtgatggaa tatgttaatg ggggcgagct gttttttccat    720 ttgtcgagag agcgggtgtt ctctgaggac cgcacacgtt tctatggtgc agaaattgtc    780
tctgccttgg actatctaca ttccggaaag attgtgtacc gtgatctcaa gttggagaat    840
ctaatgctgg acaaagatgg ccacataaaa attacagatt ttggactttg caaagaaggg    900
atcacagatg cagccaccat gaagacattc tgtggcactc cagaatatct ggcaccagag    960
gtgttagaag ataatgacta tggccgagca gtagactggt ggggcctagg ggttgtcatg   1020
tatgaaatga tgtgtgggag gttacctttc tacaaccagg accatgagaa acttttgaa   1080 ttaatattaa tggaagacat taaatttcct cgaacactct cttcagatgc aaaatcattg    1140
ctttcagggc tcttgataaa ggatccaaat aaacgccttg gtggaggacc agatgatgca   1200
```

-continued

```
aaagaaatta tgagacacag tttcttctct ggagtaaact ggcaagatgt atatgataaa    1260
aagcttgtac ctcctttaa acctcaagta acatctgaga cagatactag atattttgat     1320
gaagaattta cagctcagac tattacaata acaccacctg aaaaatatga tgaggatggt    1380
atggactgca tggacaatga gaggcggccg catttccctc aatttttccta ctctgcaagt    1440 ggacgagaat aagtctcttt cattctgcta cttcactgtc atcttcaatt tattactgaa    1500
aatgattcct ggacatcacc agtcctagct cttacacata gcaggggcac cttccgacat    1560
cccagaccag ccaagggtcc tcacccctcg ccacctttca ccctcatgaa aacacacata    1620
cacgcaaata cactccagtt tttgttttg catgaaattg tatctcagtc taaggtctca      1680
tgctgttgct gctactgtct tactatta                                      1708
```

<210> SEQ ID NO 2
<211> LENGTH: 479
<212> TYPE: PRT
<213> ORGANISM: homo sapiens

<400> SEQUENCE: 2

```
Met Ser Asp Val Thr Ile Val Lys Glu Gly Trp Val Gln Lys Arg Gly
1               5                   10                  15

Glu Tyr Ile Lys Asn Trp Arg Pro Arg Tyr Phe Leu Leu Lys Thr Asp
                20                  25                  30

Gly Ser Phe Ile Gly Tyr Lys Glu Lys Pro Gln Asp Val Asp Leu Pro
            35                  40                  45

Tyr Pro Leu Asn Asn Phe Ser Val Ala Lys Cys Gln Leu Met Lys Thr
        50                  55                  60

Glu Arg Pro Lys Pro Asn Thr Phe Ile Ile Arg Cys Leu Gln Trp Thr
65                  70                  75                  80

Thr Val Ile Glu Arg Thr Phe His Val Asp Thr Pro Glu Glu Arg Glu
                85                  90                  95

Glu Trp Thr Glu Ala Ile Gln Ala Val Ala Asp Arg Leu Gln Arg Gln
            100                 105                 110

Glu Glu Glu Arg Met Asn Cys Ser Pro Thr Ser Gln Ile Asp Asn Ile
        115                 120                 125

Gly Glu Glu Glu Met Asp Ala Ser Thr Thr His His Lys Arg Lys Thr
130                 135                 140

Met Asn Asp Phe Asp Tyr Leu Lys Leu Leu Gly Lys Gly Thr Phe Gly
145                 150                 155                 160

Lys Val Ile Leu Val Arg Glu Lys Ala Ser Gly Lys Tyr Tyr Ala Met
                165                 170                 175

Lys Ile Leu Lys Lys Glu Val Ile Ile Ala Lys Asp Glu Val Ala His
            180                 185                 190

Thr Leu Thr Glu Ser Arg Val Leu Lys Asn Thr Arg His Pro Phe Leu
        195                 200                 205

Thr Ser Leu Lys Tyr Ser Phe Gln Thr Lys Asp Arg Leu Cys Phe Val
    210                 215                 220

Met Glu Tyr Val Asn Gly Gly Glu Leu Phe Phe His Leu Ser Arg Glu
225                 230                 235                 240

Arg Val Phe Ser Glu Asp Arg Thr Arg Phe Tyr Gly Ala Glu Ile Val
                245                 250                 255

Ser Ala Leu Asp Tyr Leu His Ser Gly Lys Ile Val Tyr Arg Asp Leu
            260                 265                 270

Lys Leu Glu Asn Leu Met Leu Asp Lys Asp Gly His Ile Lys Ile Thr
        275                 280                 285
```

```
Asp Phe Gly Leu Cys Lys Glu Gly Ile Thr Asp Ala Thr Met Lys
    290                 295                 300
Thr Phe Cys Gly Thr Pro Glu Tyr Leu Ala Pro Glu Val Leu Glu Asp
305                 310                 315                 320
Asn Asp Tyr Gly Arg Ala Val Asp Trp Trp Gly Leu Gly Val Val Met
                325                 330                 335
Tyr Glu Met Met Cys Gly Arg Leu Pro Phe Tyr Asn Gln Asp His Glu
                340                 345                 350
Lys Leu Phe Glu Leu Ile Leu Met Glu Asp Ile Lys Phe Pro Arg Thr
            355                 360                 365
Leu Ser Ser Asp Ala Lys Ser Leu Leu Ser Gly Leu Leu Ile Lys Asp
    370                 375                 380
Pro Asn Lys Arg Leu Gly Gly Pro Asp Asp Ala Lys Glu Ile Met
385                 390                 395                 400
Arg His Ser Phe Phe Ser Gly Val Asn Trp Gln Asp Val Tyr Asp Lys
                405                 410                 415
Lys Leu Val Pro Pro Phe Lys Pro Gln Val Thr Ser Glu Thr Asp Thr
                420                 425                 430
Arg Tyr Phe Asp Glu Glu Phe Thr Ala Gln Thr Ile Thr Ile Thr Pro
            435                 440                 445
Pro Glu Lys Tyr Asp Glu Asp Gly Met Asp Cys Met Asp Asn Glu Arg
    450                 455                 460
Arg Pro His Phe Pro Gln Phe Ser Tyr Ser Ala Ser Gly Arg Glu
465                 470                 475

<210> SEQ ID NO 3
<211> LENGTH: 478
<212> TYPE: PRT
<213> ORGANISM: homo sapiens

<400> SEQUENCE: 3

Ser Asp Val Thr Ile Val Lys Glu Gly Trp Val Gln Lys Arg Gly Glu
1               5                   10                  15
Tyr Ile Lys Asn Trp Arg Pro Arg Tyr Phe Leu Leu Lys Thr Asp Gly
                20                  25                  30
Ser Phe Ile Gly Tyr Lys Glu Lys Pro Gln Asp Val Asp Leu Pro Tyr
            35                  40                  45
Pro Leu Asn Asn Phe Ser Val Ala Lys Cys Gln Leu Met Lys Thr Glu
    50                  55                  60
Arg Pro Lys Pro Asn Thr Phe Ile Ile Arg Cys Leu Gln Trp Thr Thr
65                  70                  75                  80
Val Ile Glu Arg Thr Phe His Val Asp Thr Pro Glu Glu Arg Glu Glu
                85                  90                  95
Trp Thr Glu Ala Ile Gln Ala Val Ala Asp Arg Leu Gln Arg Gln Glu
                100                 105                 110
Glu Glu Arg Met Asn Cys Ser Pro Thr Ser Gln Ile Asp Asn Ile Gly
            115                 120                 125
Glu Glu Glu Met Asp Ala Ser Thr Thr His His Lys Arg Lys Thr Met
    130                 135                 140
Asn Asp Phe Asp Tyr Leu Lys Leu Leu Gly Lys Gly Thr Phe Gly Lys
145                 150                 155                 160
Val Ile Leu Val Arg Glu Lys Ala Ser Gly Lys Tyr Tyr Ala Met Lys
                165                 170                 175
Ile Leu Lys Lys Glu Val Ile Ile Ala Lys Asp Glu Val Ala His Thr
                180                 185                 190
```

-continued

```
Leu Thr Glu Ser Arg Val Leu Lys Asn Thr Arg His Pro Phe Leu Thr
        195                 200                 205
Ser Leu Lys Tyr Ser Phe Gln Thr Lys Asp Arg Leu Cys Phe Val Met
    210                 215                 220
Glu Tyr Val Asn Gly Gly Glu Leu Phe Phe His Leu Ser Arg Glu Arg
225                 230                 235                 240
Val Phe Ser Glu Asp Arg Thr Arg Phe Tyr Gly Ala Glu Ile Val Ser
                245                 250                 255
Ala Leu Asp Tyr Leu His Ser Gly Lys Ile Val Tyr Arg Asp Leu Lys
                260                 265                 270
Leu Glu Asn Leu Met Leu Asp Lys Asp Gly His Ile Lys Ile Thr Asp
            275                 280                 285
Phe Gly Leu Cys Lys Glu Gly Ile Thr Asp Ala Ala Thr Met Lys Thr
        290                 295                 300
Phe Cys Gly Thr Pro Glu Tyr Leu Ala Pro Glu Val Leu Glu Asp Asn
305                 310                 315                 320
Asp Tyr Gly Arg Ala Val Asp Trp Trp Gly Leu Gly Val Val Met Tyr
                325                 330                 335
Glu Met Met Cys Gly Arg Leu Pro Phe Tyr Asn Gln Asp His Glu Lys
            340                 345                 350
Leu Phe Glu Leu Ile Leu Met Glu Asp Ile Lys Phe Pro Arg Thr Leu
        355                 360                 365
Ser Ser Asp Ala Lys Ser Leu Leu Ser Gly Leu Leu Ile Lys Asp Pro
370                 375                 380
Asn Lys Arg Leu Gly Gly Gly Pro Asp Asp Ala Lys Glu Ile Met Arg
385                 390                 395                 400
His Ser Phe Phe Ser Gly Val Asn Trp Gln Asp Val Tyr Asp Lys Lys
                405                 410                 415
Leu Val Pro Pro Phe Lys Pro Gln Val Thr Ser Glu Thr Asp Thr Arg
            420                 425                 430
Tyr Phe Asp Glu Glu Phe Thr Ala Gln Thr Ile Thr Ile Thr Pro Pro
        435                 440                 445
Glu Lys Tyr Asp Glu Asp Gly Met Asp Cys Met Asp Asn Glu Arg Arg
    450                 455                 460
Pro His Phe Pro Gln Phe Ser Tyr Ser Ala Ser Gly Arg Glu
465                 470                 475
```